(12) United States Patent
Jerry

(10) Patent No.: US 12,193,941 B2
(45) Date of Patent: Jan. 14, 2025

(54) TIBIAL-TRAY SYSTEM

(71) Applicant: Gerald J. Jerry, Grosse Pointe, MI (US)

(72) Inventor: Gerald J. Jerry, Grosse Pointe, MI (US)

( * ) Notice: Subject to any disclaimer, the term of this patent is extended or adjusted under 35 U.S.C. 154(b) by 208 days.

(21) Appl. No.: 17/726,168

(22) Filed: Apr. 21, 2022

(65) Prior Publication Data

US 2022/0338996 A1    Oct. 27, 2022

Related U.S. Application Data

(60) Provisional application No. 63/320,005, filed on Mar. 15, 2022, provisional application No. 63/178,614, filed on Apr. 23, 2021.

(51) Int. Cl.
*A61F 2/38* (2006.01)
*A61F 2/30* (2006.01)

(52) U.S. Cl.
CPC ............ *A61F 2/389* (2013.01); *A61F 2/3886* (2013.01); *A61F 2002/30329* (2013.01); *A61F 2002/30332* (2013.01); *A61F 2002/30492* (2013.01); *A61F 2002/30518* (2013.01); *A61F 2002/30553* (2013.01); *A61F 2002/30616* (2013.01); *A61F 2250/006* (2013.01)

(58) Field of Classification Search
CPC .................. A61F 2002/30492; A61F 2/3886
See application file for complete search history.

(56) References Cited

U.S. PATENT DOCUMENTS

| | | | |
|---|---|---|---|
| 6,004,352 A | 12/1999 | Buni | |
| 6,926,738 B2 | 8/2005 | Wyss | |
| 7,288,115 B2 | 10/2007 | Hawkins | |
| 8,092,545 B2 | 1/2012 | Coon et al. | |
| 8,163,028 B2 | 4/2012 | Metzger et al. | |
| 9,044,327 B2 | 6/2015 | Liu et al. | |
| 9,585,758 B2 | 3/2017 | Metzger et al. | |
| 9,675,464 B2 | 6/2017 | Jerry | |
| 2001/0003803 A1* | 6/2001 | Leclercq ............... | A61F 2/3886 623/20.29 |
| 2003/0009232 A1* | 1/2003 | Metzger ............... | A61F 2/3868 623/20.29 |
| 2008/0167722 A1 | 7/2008 | Metzger et al. | |
| 2008/0243258 A1* | 10/2008 | Sancheti ............... | A61F 2/3886 623/20.15 |
| 2009/0264894 A1 | 10/2009 | Wasielewski | |
| 2010/0312351 A1* | 12/2010 | Belcher ................. | A61F 2/3094 623/20.32 |

(Continued)

FOREIGN PATENT DOCUMENTS

WO    WO-2012058560 A1 *  5/2012   ........... A61F 2/3868
WO       2017155995 A1      9/2017

*Primary Examiner* — Melanie R Tyson
*Assistant Examiner* — Yasniary De La Caridad Morales
(74) *Attorney, Agent, or Firm* — Brooks Kushman P.C.

(57) ABSTRACT

A tibial-tray system may include a tibial tray and a spline configured to extend proximally from the tibial tray and guide a femoral component of a knee system. The tibial-tray system may also include an adapter configured for attachment to the tibial tray and the spline. A distal end of the adapter may have a position relative to a position of a proximal end of the adapter such that the spline extends upward from the tibial tray at a predetermined position.

18 Claims, 20 Drawing Sheets

(56) References Cited

U.S. PATENT DOCUMENTS

| | | | |
|---|---|---|---|
| 2011/0125202 A1* | 5/2011 | Ries | A61F 2/461 606/86 R |
| 2014/0039636 A1 | 2/2014 | Kurtz | |
| 2014/0243988 A1* | 8/2014 | Lenz | A61F 2/389 623/20.27 |
| 2014/0371865 A1 | 12/2014 | Jordan et al. | |
| 2019/0076271 A1* | 3/2019 | Gilson | A61F 2/4684 |
| 2020/0246150 A1* | 8/2020 | Matyas | A61F 2/3859 |
| 2023/0293104 A1* | 9/2023 | Gross | A61F 2/38 623/20.32 |

\* cited by examiner

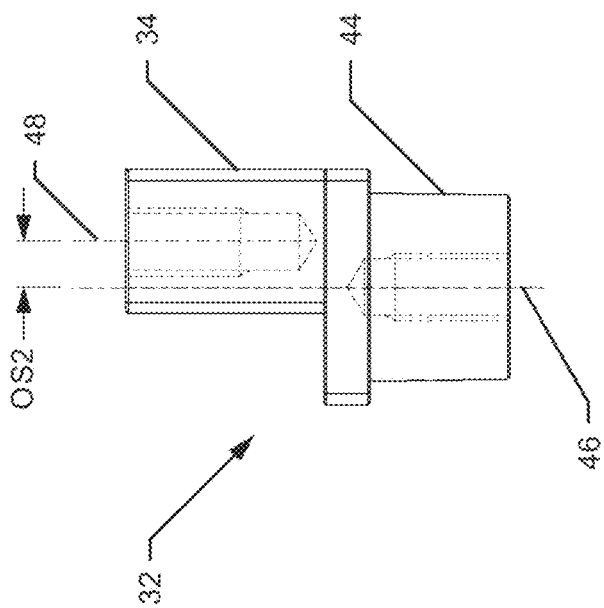
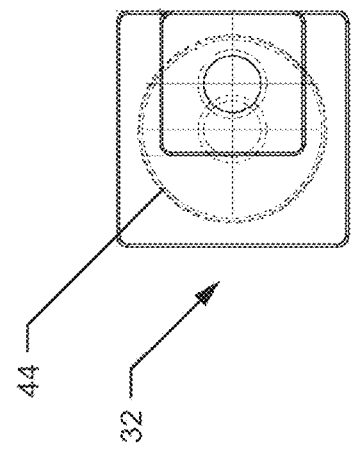
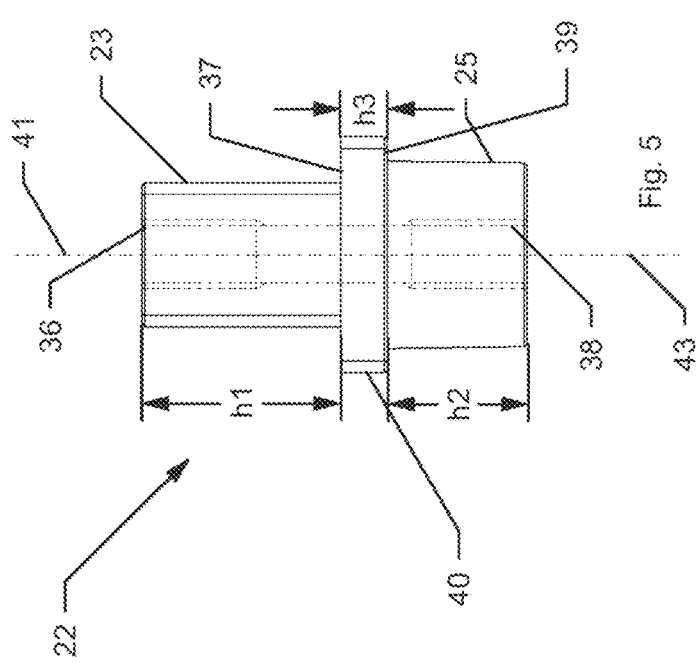
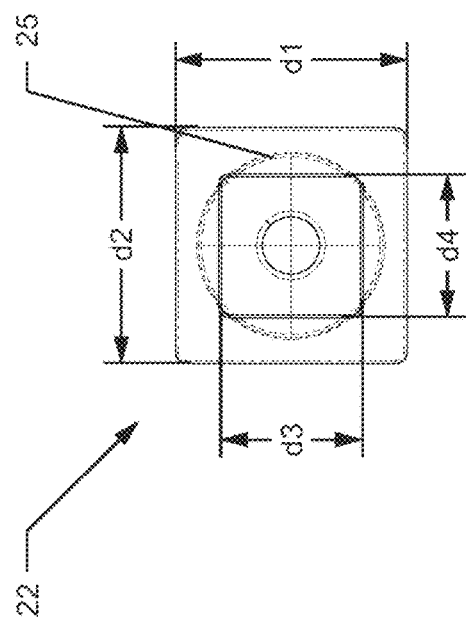
Fig. 5
Fig. 6

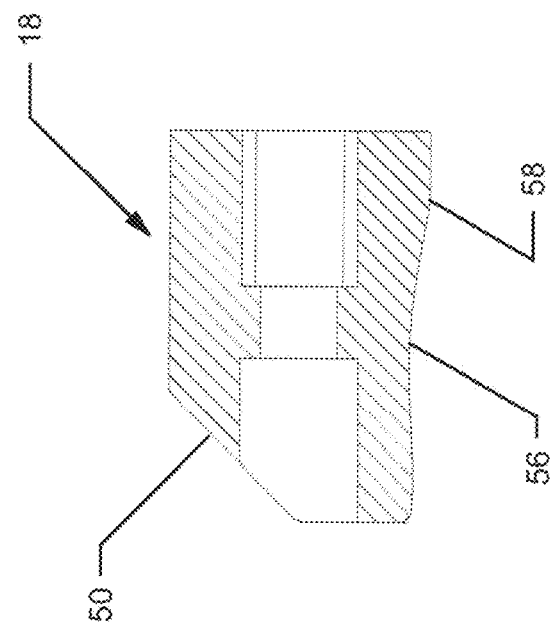
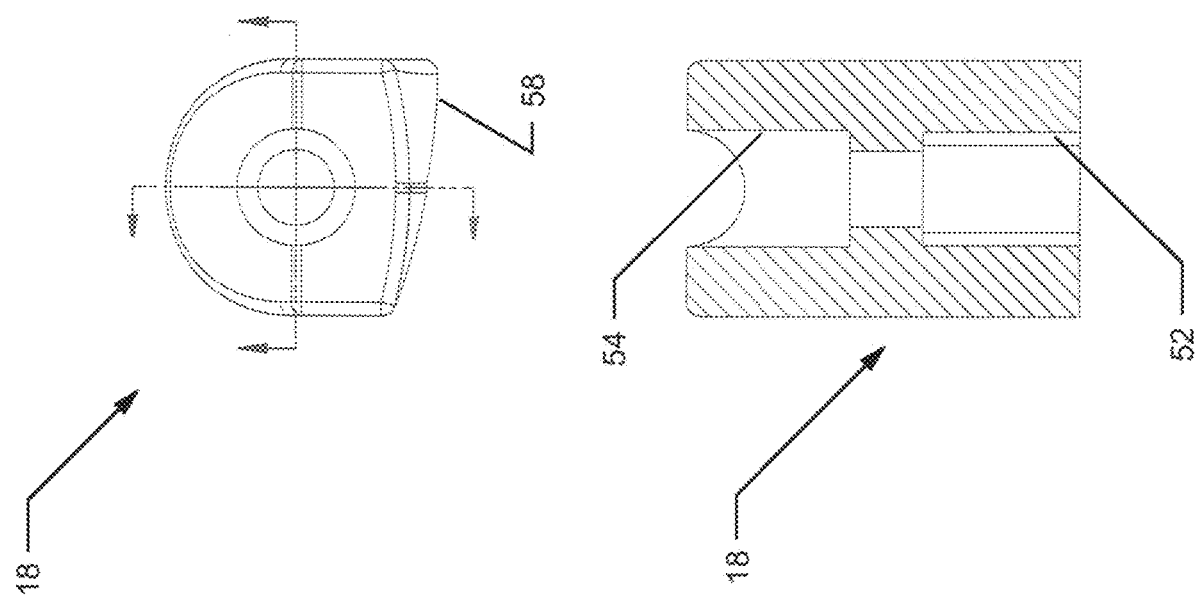
Fig. 7

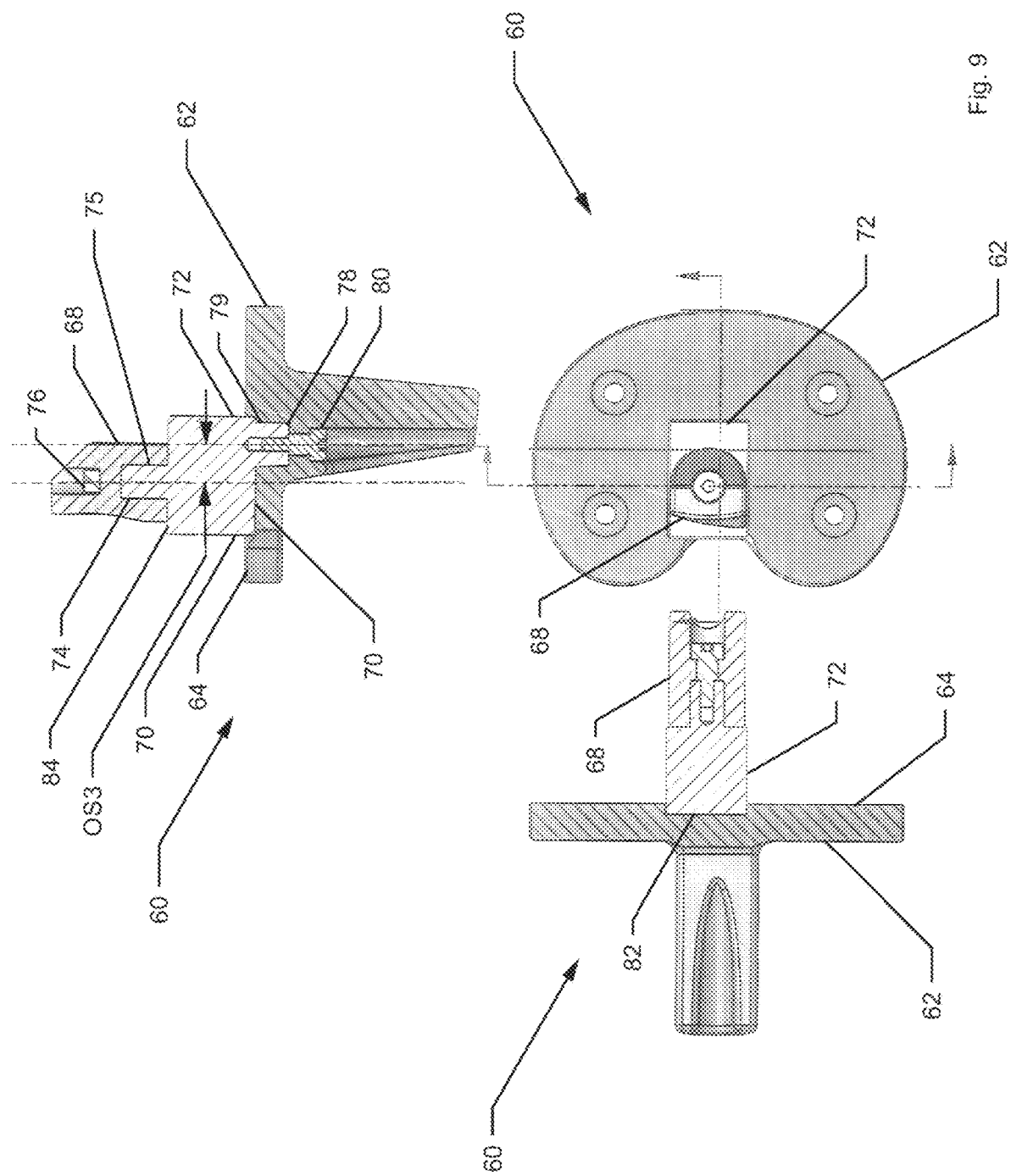

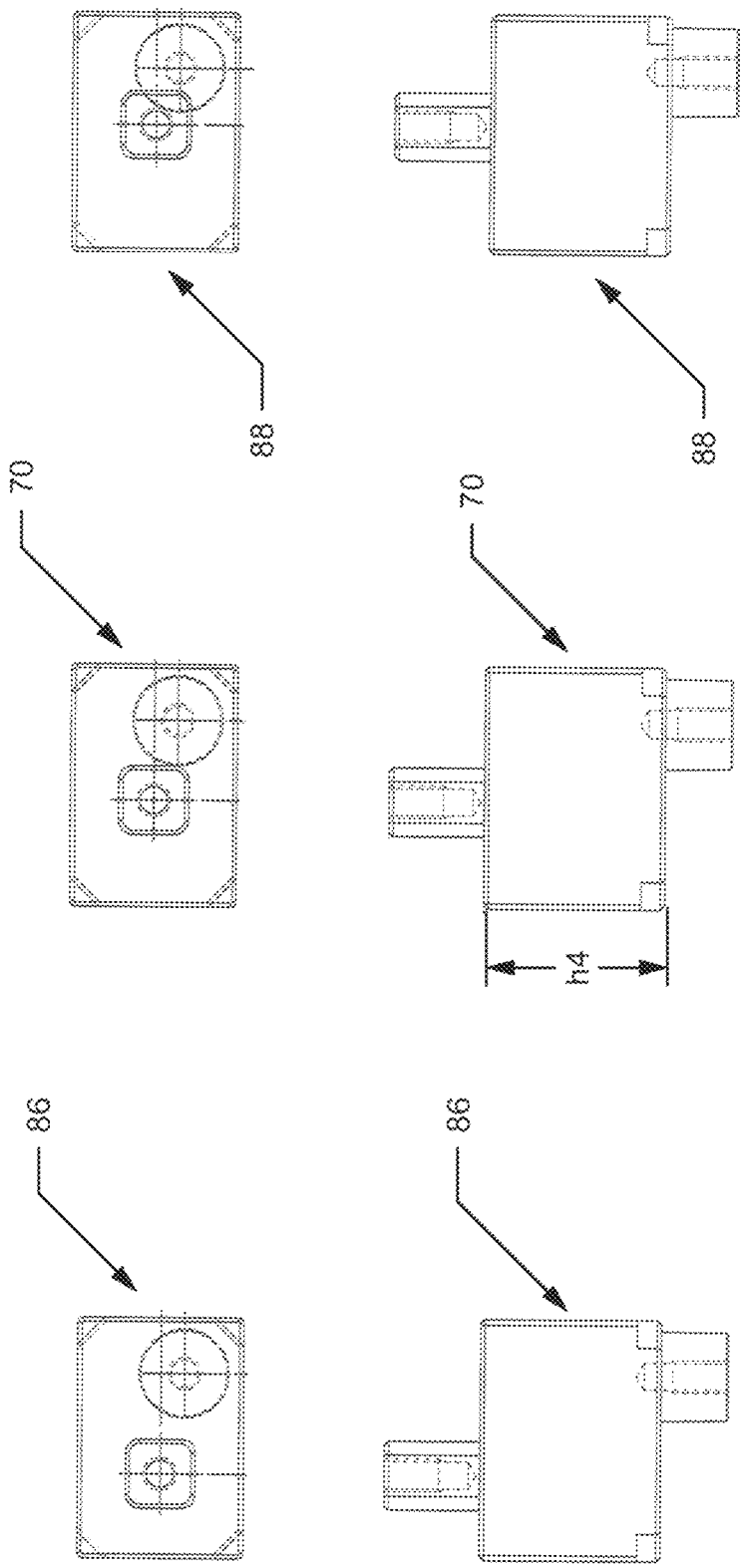

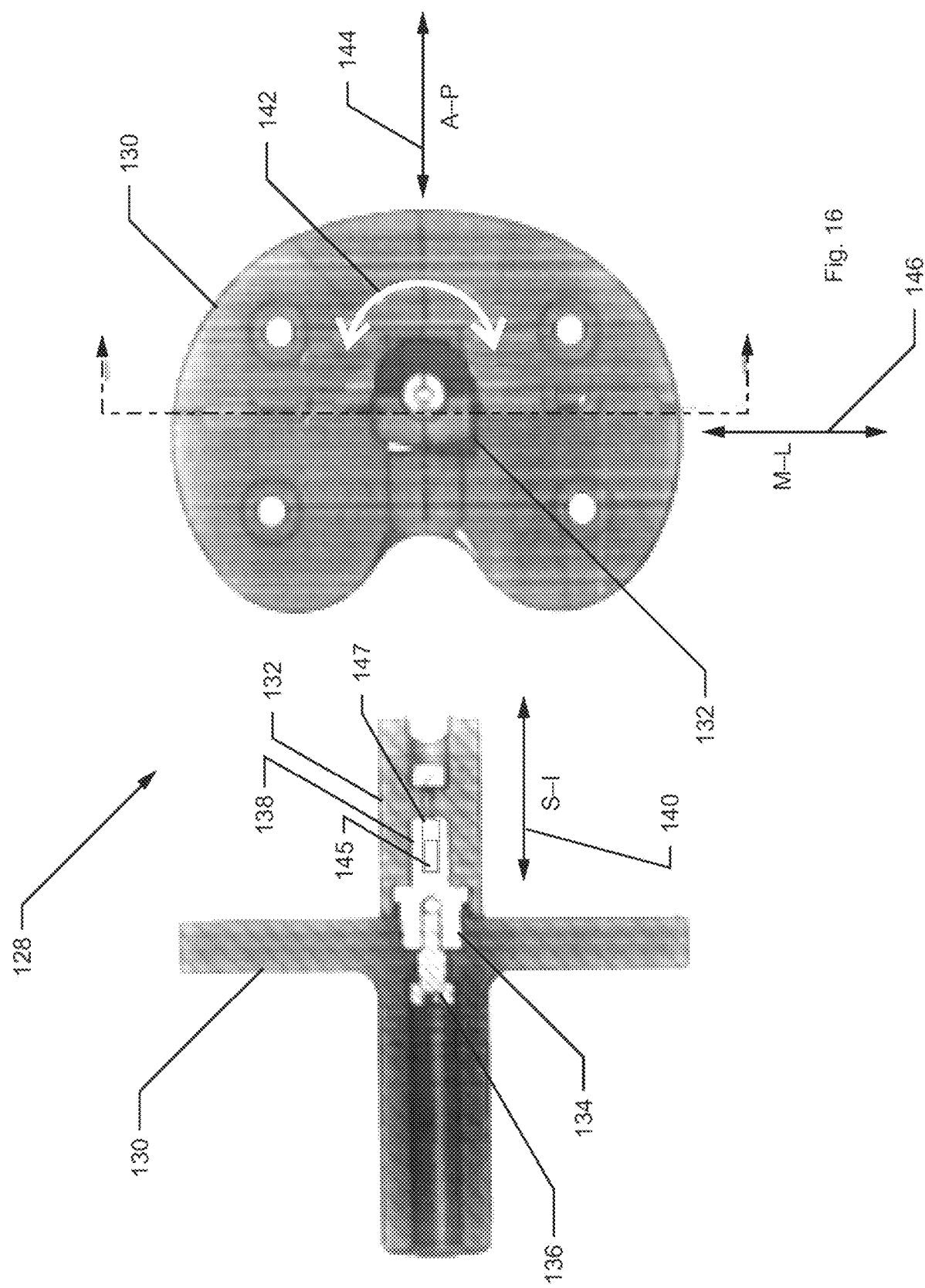

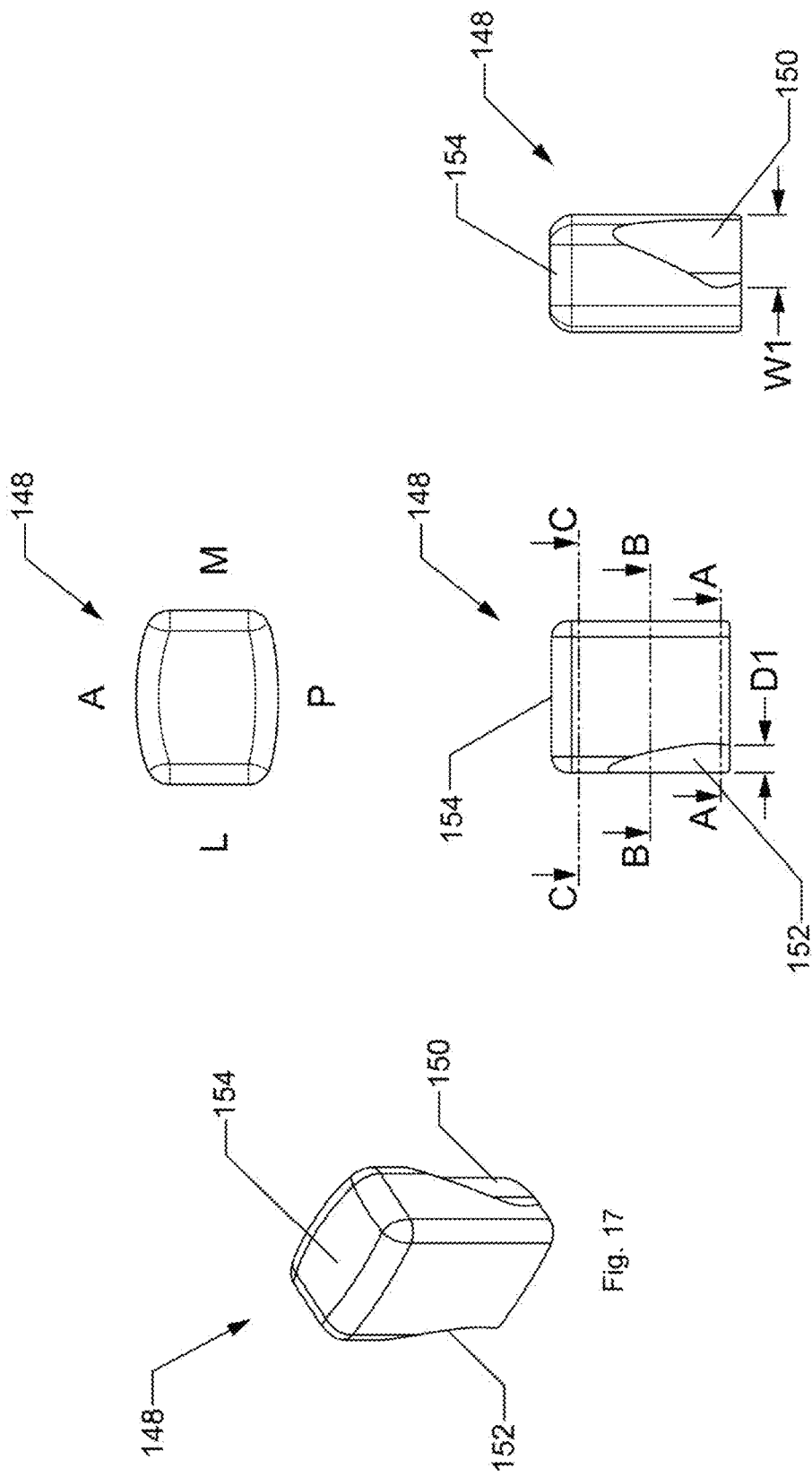

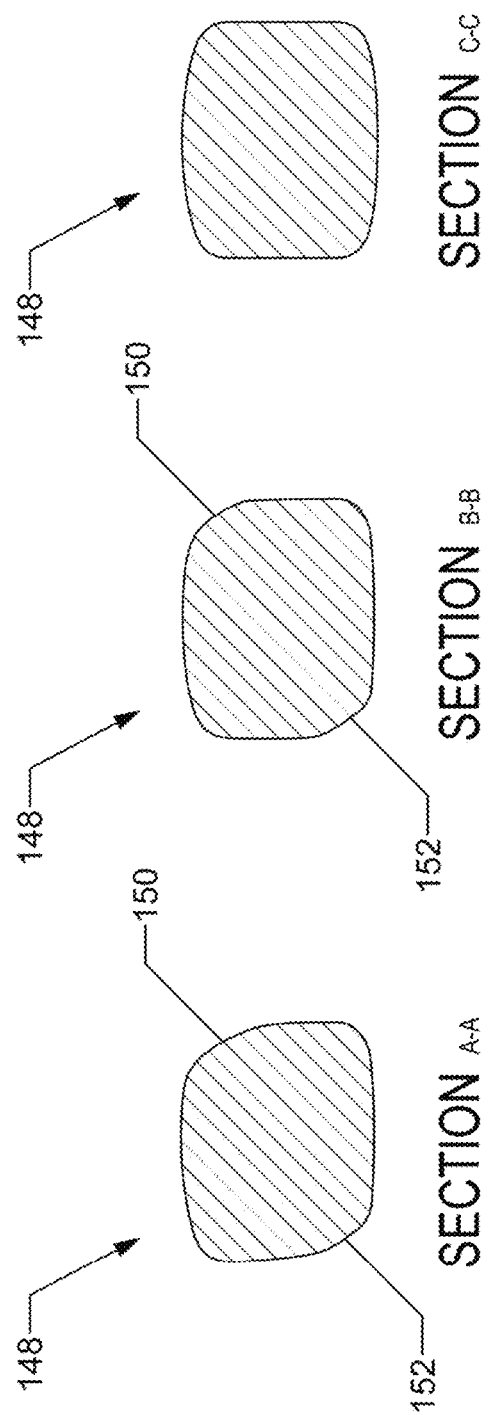

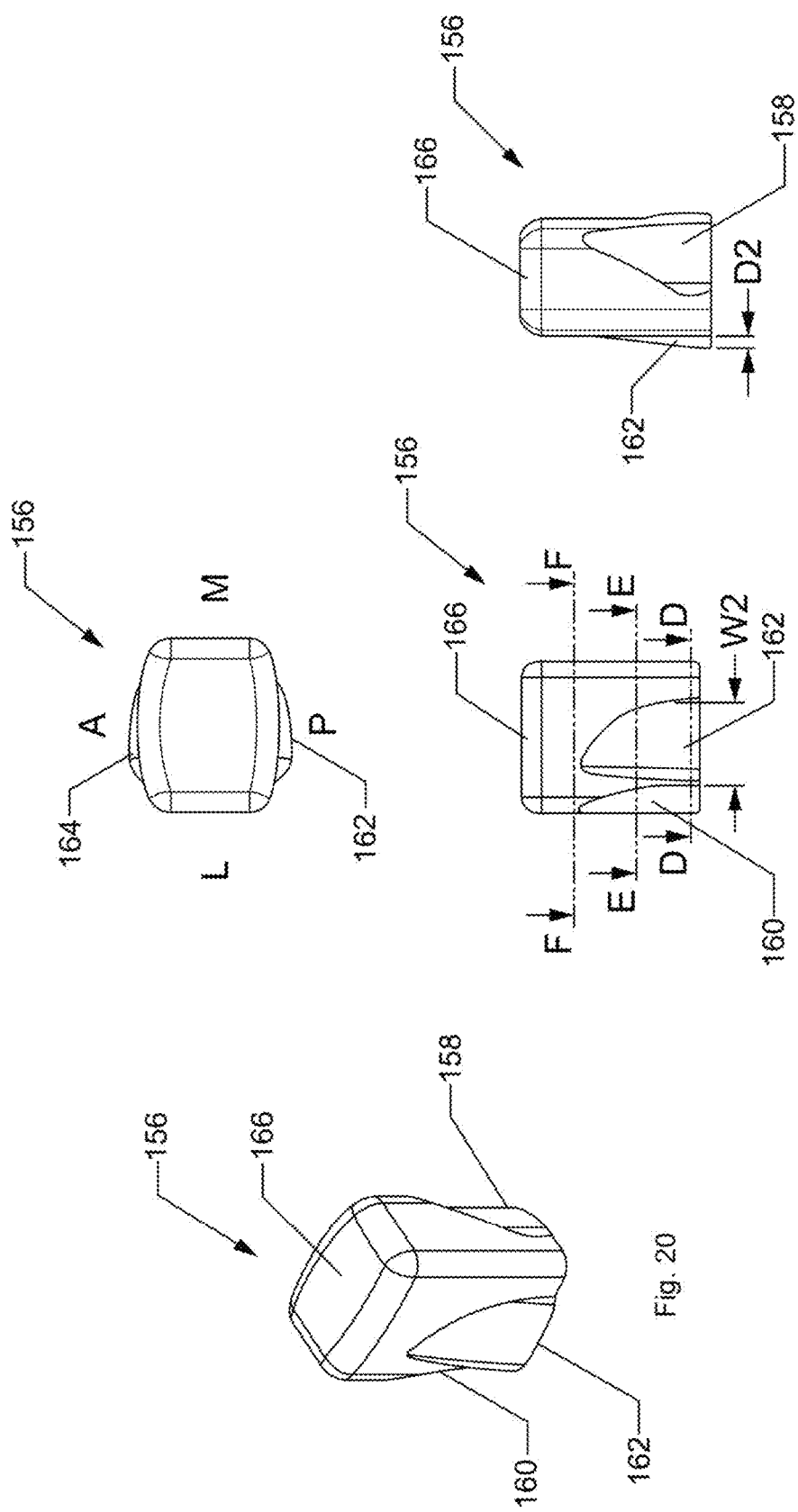

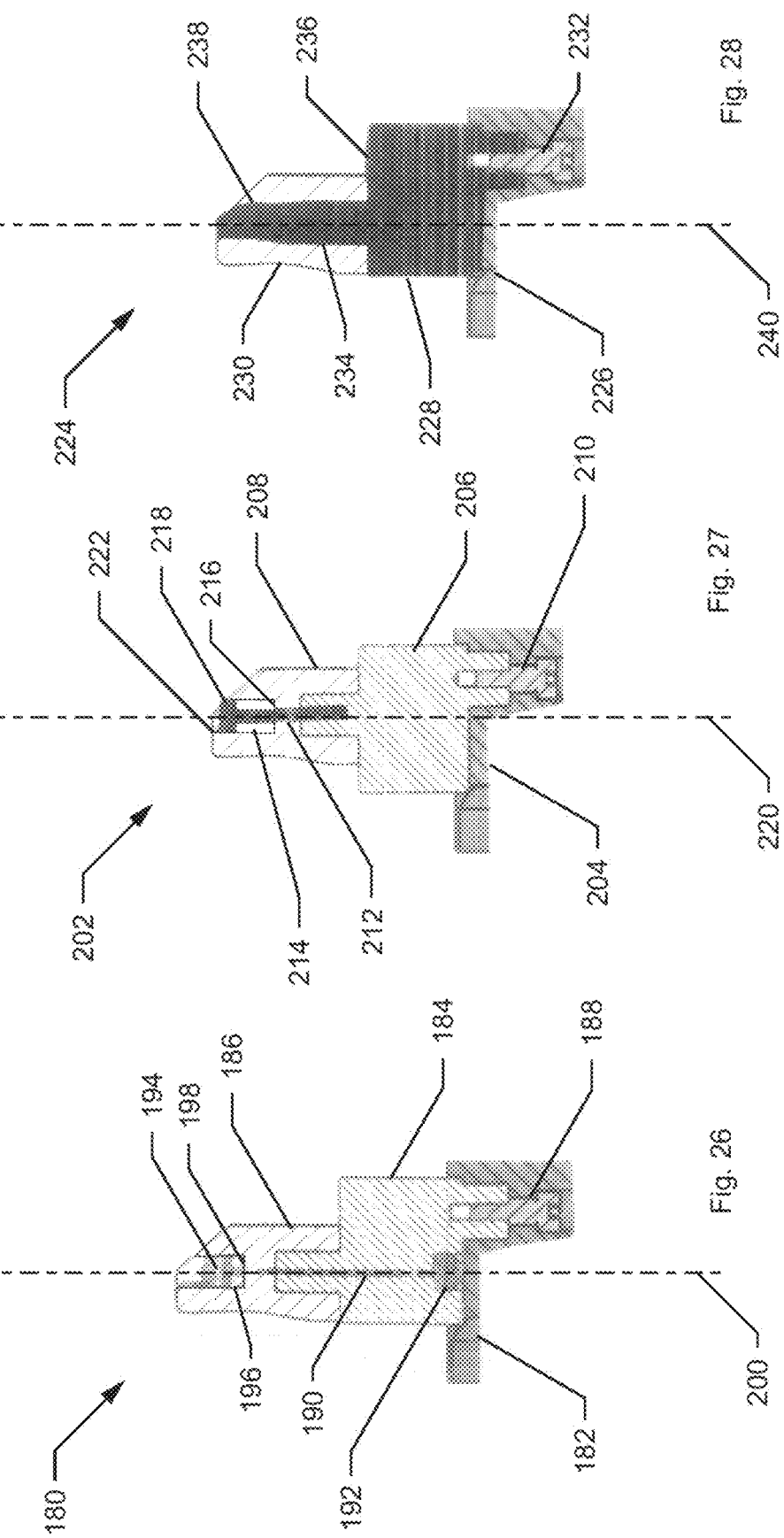

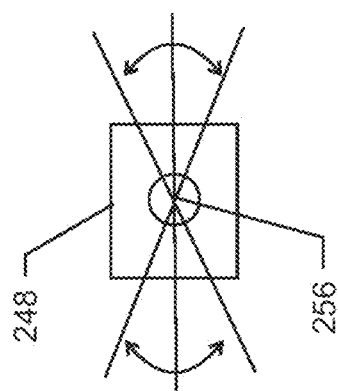
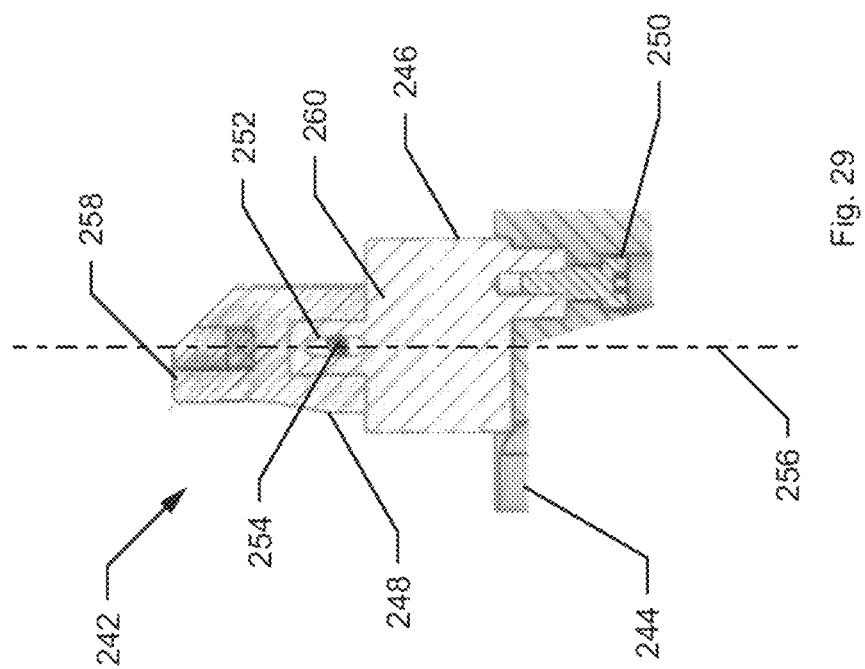

TIBIAL-TRAY SYSTEM

CROSS-REFERENCE TO RELATED APPLICATIONS

This application claims the benefit of U.S. provisional application Ser. No. 63/178,614 filed Apr. 23, 2021, and claims the benefit of U.S. provisional application Ser. No. 63/320,005 filed Mar. 15, 2022, the disclosures of which are hereby incorporated in their entirety by reference herein.

TECHNICAL FIELD

The present disclosure relates to a surgically implantable tibial-tray system.

BACKGROUND

Although human physiology is often reasonably consistent across a wide variety of people, everyone is, at least to some extent, unique. For example, some basic physical characteristics of a femur or tibia may be similar for much of the population, but differences in size, shape, and strength may vary widely from one person to the next. Historically, orthopedic medical devices have been manufactured in a wide variety of sizes to accommodate differences between the patients. The result is that many of these devices—especially those at the extremes of the range—are largely unused. This creates unwanted excess inventory and increases costs for manufacturers and medical facilities alike.

In addition, some orthopedic implants, such as a tibial-tray system, have many different features that can be made larger or smaller—e.g., the area of the tray itself, the size and position of a notch to accommodate a posterior cruciate ligament, the size and position of a stem extending distally from the bottom of the tray, and the size and position of a spline extending proximally from the tray to guide a femoral component. Therefore, a need exists for a tibial-tray system that is modular in nature and allows the needs of different patients to be addressed by providing individual, modular components that can be sized and positioned intra-operatively as desired, without the need for a complete system to be made for each desired size and shape.

SUMMARY

Embodiments described herein include a tibial-tray system having a modular configuration with a tray, a spline extending proximally from the tray and configured to guide a femoral component of a knee system, and a locking device, which may be in the form of an adapter attached to the spline and the tray. The tray may have a central platform onto which the spline is positioned.

At least some embodiments described herein may include a locking device configured as a female-to-female adapter that is straight—i.e., provides a neutral position for the spline—while others may include an adapter having an offset to position the spline at a desired location—for example, at a particular anterior-posterior or medial-lateral position on the tray. The adapter may include a taper—for example, a Morse taper—on the outside surface of one or both of its ends to engage the tray on its distal end and the spline on its proximal end. Other adapters may be male-to-male, male-to-female, or female-to-male.

In at least some embodiments described herein a tibial-tray system may be configured such that an adapter includes internal threads on one or both ends so that the spline, the tray, or both can be primarily or secondarily secured with a threaded fastener. The threaded fastener may be used in conjunction with an adapter having a tapered outside surface as described above, or it may be used exclusively for adapters that do not have a tapered outside surface.

At least some embodiments described herein may include an adapter with a tapered outside surface on its distal end to engage a mating taper in the tibial tray, while having a non-tapered proximal end to allow the spline to rotate, piston up and down, or both. Adapters such as described herein may be made from a titanium alloy, tantalum, stainless steel, cobalt chromium, polymers, or other biocompatible materials. The splines may be made from a polymer, such as cross-linked polyethylene or polyether ether ketone (PEEK), or they may be made from a ceramic or some other material effective to perform the desired function. A surface of the spline may engage with a femoral component cam and may be provided with a straight or curved surface, and in some embodiments may include a distal eminence to facilitate a natural motion, rotation, or both of the femoral component during flexion and through the range of motion.

In at least some embodiments, the adapter may include a raised center portion that effectively positions the spline further upward—i.e., proximally—via soma-like thicknesses, stacking thicknesses, unique customized thicknesses, or some combination of these. This may allow a single spline configuration to be used with patients requiring different proximal—distal positioning of the spline—through different adapter thicknesses—thereby providing a significant inventory reduction and cost savings. Even though multiple adapters may be needed, a metal adapter whose packaging is opened, but which is not used in the surgery, can be resterilized and available for use in a subsequent surgery. This is in contrast to a polymeric spline, which cannot be resterilized; therefore, once its package is opened, the spline must be implanted or discarded. In addition, components stored in sterile packaging have a finite shelf life—typically between one and five years—so that even if the component is not opened, its useful life will eventually expire, and thereafter it cannot be used. Metal components can be resterilized after expiration, whereas polymeric components cannot; this creates significant waste, burdensome cost and increased medical expenses.

In addition to the inventory and cost savings described above, embodiments described herein may provide significant clinical advantages as well. For example, a knee implant using a tibial-tray system such as described herein may provide the ability to adjust the anterior—posterior location, the medial—lateral location, or both, of the spline intra-operatively—i.e., in real time while the surgery is being performed. This allows the surgeon to assess the requirements of the patient in a way that is not possible by remotely viewing x-rays or other images. This system is more likely to result in optimal pressure mechanics of the knee joint, soft-tissue balancing, and less postoperative pain. It may also improve long-term outcomes because an adjustable spline affords intra-operative assessment and adjustment to improve appropriate kinematics.

Embodiments described herein may include a tibial-tray system with a modular spline that affords adjustment in multiple degrees of motion. For example, the adjustment may be available in anterior-posterior translation, medial-lateral translation, superior-inferior translation, rotation about the superior-inferior axis, or some combination of these.

Embodiments described herein may include a tibial-tray system having a tibial tray and a spline configured to extend proximally from the tibial tray and guide a femoral component of a knee system. The tibial-tray system may also include an adapter having a distal end configured for attachment to the tibial tray and a proximal end configured for attachment to the spline. The distal end may have a position relative to a position of the proximal end such that the spline extends upward from the tibial tray at a predetermined position when the distal end of the adapter is attached to the tibial tray and the proximal end of the adapter is attached to the spline.

Embodiments described herein may include a tibial-tray system having a tibial tray and a spline configured to extend proximally from the tibial tray and guide a femoral component of a knee system. The tibial-tray system may also include an adapter including a platform having a proximal face with a proximal member extending therefrom and a distal face with a distal member extending therefrom. The proximal member may be configured for attachment to the spline and the distal member may be configured for attachment to the tibial tray. The adapter may be configured such that a relative position between the proximal member and the distal member disposes the spline at a predetermined position relative to the tibial tray when the adapter is attached to the spline and the tibial tray.

Embodiments described herein may include a tibial-tray system having a tibial tray and a spline configured to extend proximally from the tibial tray and guide a femoral component of a knee system. The tibial-tray system may also include an adapter configured to be positioned between the tibial tray and the spline such that a first portion of the adapter is attachable to the spline and a second portion of the adapter is attachable to the tibial tray to dispose the spline at a predetermined position relative to the tibial tray when the adapter is attached to the spline and the tibial tray.

BRIEF DESCRIPTION OF THE DRAWINGS

FIG. 5 shows top and side views of a neutral-position adapter in accordance with embodiments described herein;

FIG. 6 shows top and side views of an offset-position adapter in accordance with embodiments described herein;

FIG. 7 shows a top view and two sectional views of a spline in accordance with embodiments described herein;

FIG. 9 shows three views of the tibial-tray system shown in FIG. 8 having a neutral-position adapter;

FIG. 10 shows top and side views of a posterior-offset adapter in accordance with embodiments described herein;

FIG. 11 shows top and side views of a neutral-position adapter in accordance with embodiments described herein;

FIG. 12 shows top and side views of an anterior-offset adapter in accordance with embodiments described herein;

FIG. 16 shows two views of a tibial-tray system in accordance with embodiments described herein having a spline movable relative to an adapter;

FIG. 17 shows a perspective view of a spline configured with relief areas in a distal portion;

FIG. 18 shows top, front, and side views of the spline shown in FIG. 17;

FIG. 19 shows three sectional views of the spline shown in FIG. 18;

FIG. 20 shows a perspective view of a spline configured with relief areas and projections on the anterior and posterior surfaces;

FIG. 21 shows top, front, and side views of the spline shown in FIG. 20;

FIG. 26 shows a tibial-tray system in accordance with embodiments described herein having an adapter and a spline configured with a constraint arrangement for limited movement of the spline relative to the adapter;

FIG. 27 shows a tibial-tray system in accordance with embodiments described herein having an adapter and a spline configured with a different constraint arrangement for limited movement of the spline relative to the adapter;

FIG. 28 shows a tibial-tray system in accordance with embodiments described herein having an adapter in the spline configured for movement relative to the adapter;

FIG. 29 shows a tibial-tray system in accordance with embodiments described herein having an adapter and a spline configured with a different constraint arrangement for limited movement of the spline relative to the adapter; and FIG. 30 shows a schematic representation of the movement of the spline shown in FIG. 29 relative to the adapter.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
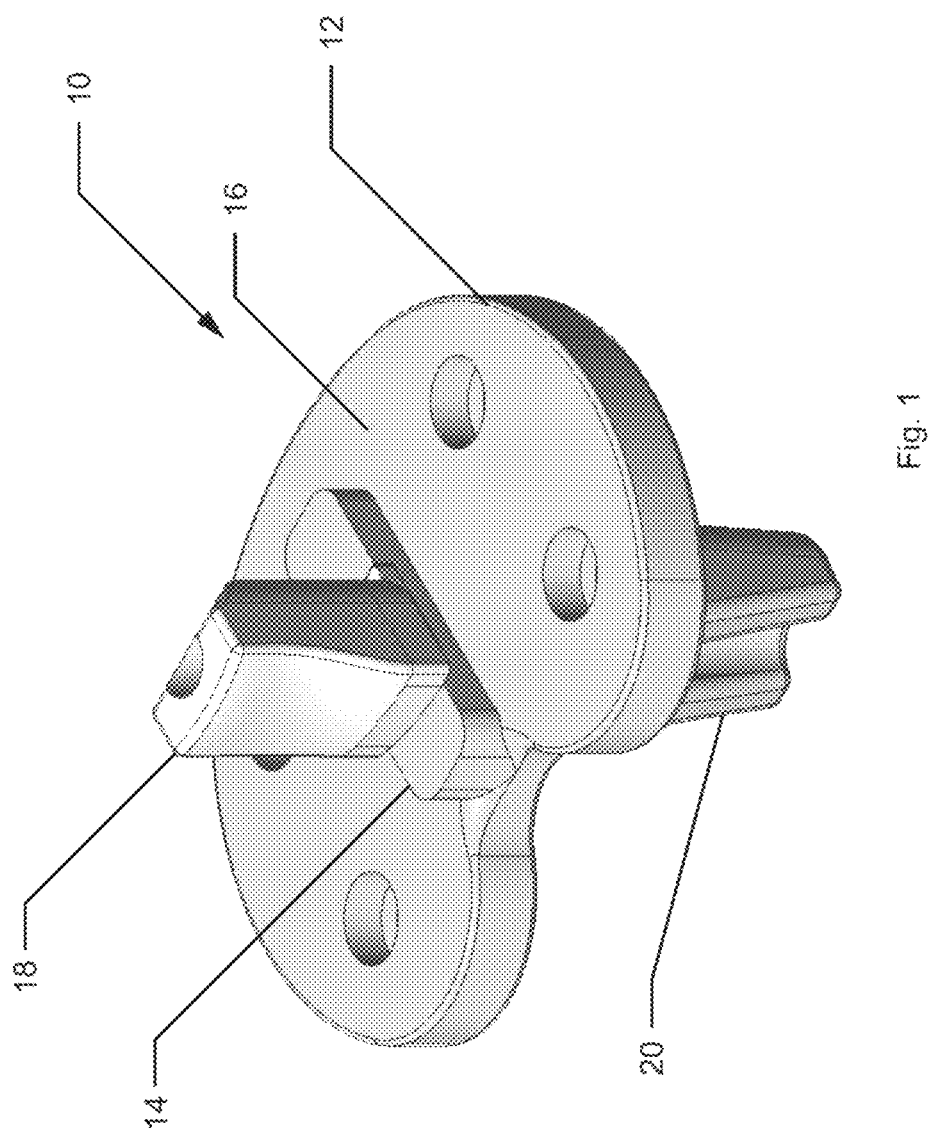
FIG. 1 shows a perspective view of a tibial-tray system in accordance with embodiments described herein.

FIG. 1 shows a portion of a tibial-tray system 10 in accordance with embodiments described herein. The system 10 includes a tibial tray 12 having a raised central portion 14 on a proximal surface 16 of the tray 12. The raised central portion 14 is shown partially schematically and may be configured to cooperate with a polymeric tibial insert, for example, through a dovetail or other type of fastening arrangement. The tray 12 and tibial insert may be configured for fixed attachment, or the tibial insert may be movable relative to the tray 12. Also shown in FIG. 1 is a spline 18 extending proximally from the raised central portion 14 of the tibial tray 12. In the embodiment shown in FIG. 1, the tibial tray 12 has a post 20 configured to be positioned within the patient's tibia to help stabilize the tray 12.

Figure 2:
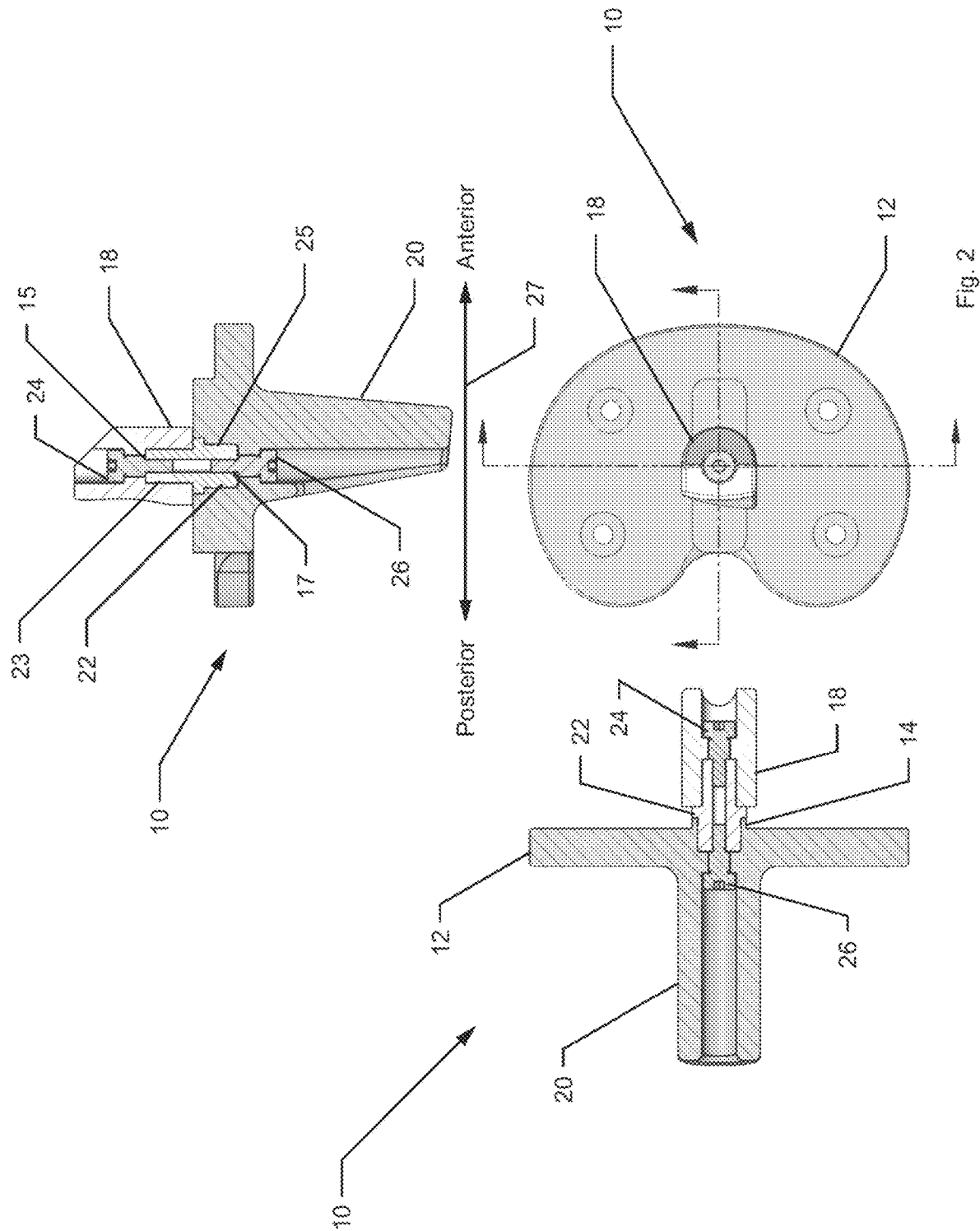
FIG. 2 shows three views of the tibial-tray system shown in FIG. 1 having a neutral-position adapter.

FIG. 2 shows a top and two sectional views of the tibial-tray system 10. Visible in the two sectional views is an adapter 22. The adapter 22 includes a first portion, or proximal end 23, and a second portion, or distal end 25. As used herein, terms such as proximal, distal, superior, inferior, anterior, posterior, medial, lateral, and other terms indicating a position relative to a patient, refer to the component, element, feature, etc. as they are intended to be oriented when implanted in a patient. As explained in more detail in conjunction with FIGS. 5 and 6, the adapter 22 is configured with a taper, such as a Morse taper, on its distal end 25 so that it fits securely into a tapered aperture in the tibial tray 12. In the embodiment shown in FIG. 2, the proximal end 23 of the adapter 22 is not tapered; it is rectangular and configured to mate with a rectangular aperture in the spline 18.

In the embodiment shown in FIG. 2, the tibial-tray system 10 includes two threaded fasteners 24, 26, which in this embodiment are shoulder bolts. The threaded fastener 24 is positioned in an aperture 15 of the proximal end 23 and helps to further secure the spline 18 to the proximal end 23 of the adapter 22. Similarly, the threaded fastener 26 is positioned in an aperture 17 of the distal end 25 and helps to further secure the adapter 22 to the tibial tray 12. In this embodiment, the fasteners 24, 26 are threaded fasteners, such as shoulder bolts. In other embodiments, however, different types of fasteners may be used, such as press-fit, bonded, or fusion fasteners. In the embodiment shown in FIG. 2, the adapter orients the spline 18 in a neutral anterior—posterior (A-P) position, the direction of which is indicated by the posterior—anterior line 27 between the top and side views. This is explained in more detail below in conjunction with FIG. 5.

Figure 3:
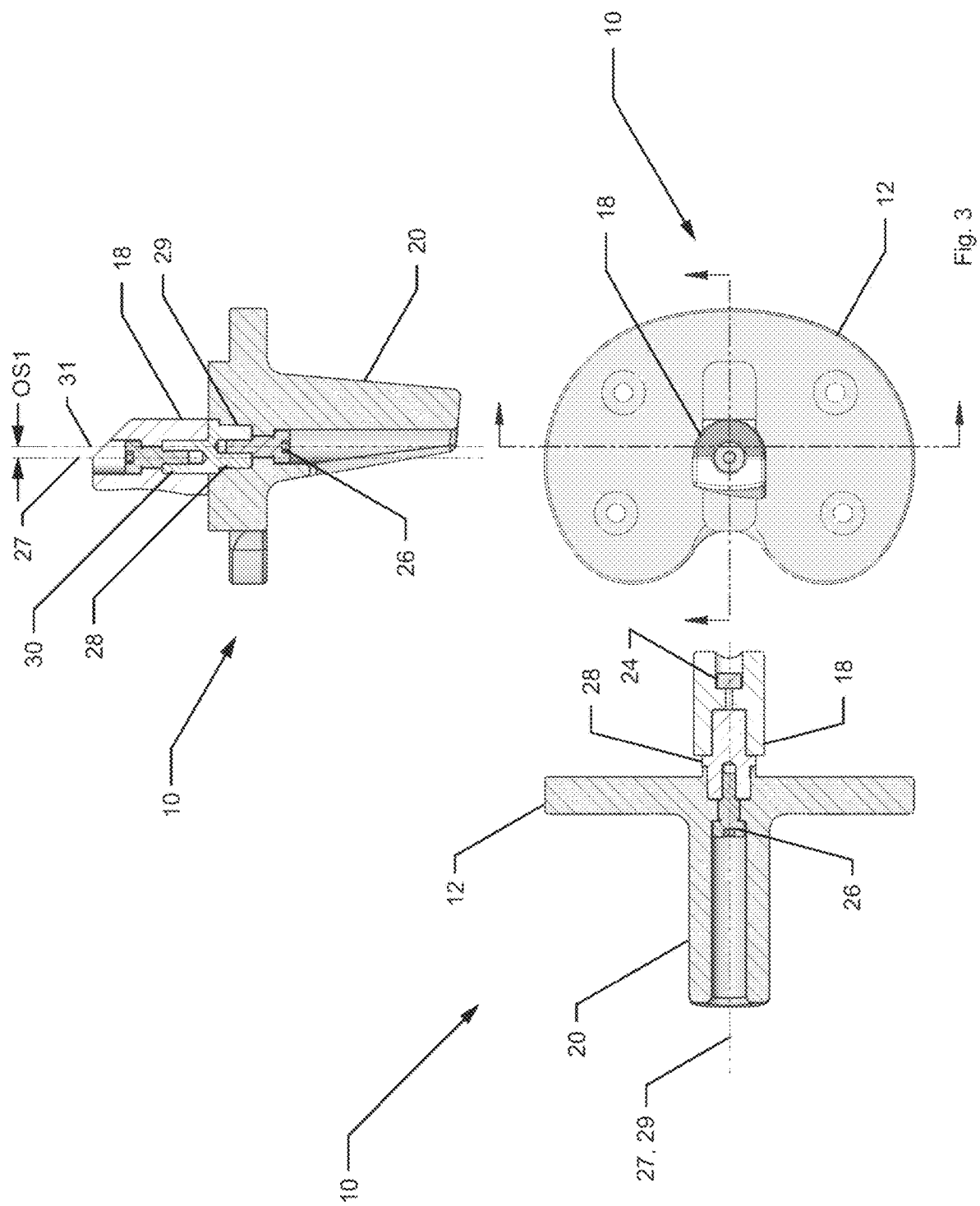
FIG. 3 shows three views of the tibial-tray system shown in FIG. 1 having a posterior-offset adapter.

In the embodiment shown in FIG. 3, the tibial-tray system 10 is fitted with a posterior-offset adapter 28. More specifically, a proximal end 30 of the adapter 28 defines a first superior-inferior axis 27, and a distal end 29 of the adapter 28 defines a second superior-inferior axis 31. The first superior-inferior axis 27 is offset by a predetermined distance of OS1, which in this embodiment is 2 mm, from the second superior-inferior axis 29 in the posterior direction. The upper view in FIG. 3 shows a section of the tibial tray system 10 viewed in a sagittal plane. The left most view in FIG. 3 shows a section of the tibial tray system 10 viewed in a coronal plane. As shown in this view, the first and second superior-inferior axes 27, 29 are coincident, indicating that the adapter 28 is neutral in the medial-lateral (M-L) direction.

Figure 4:
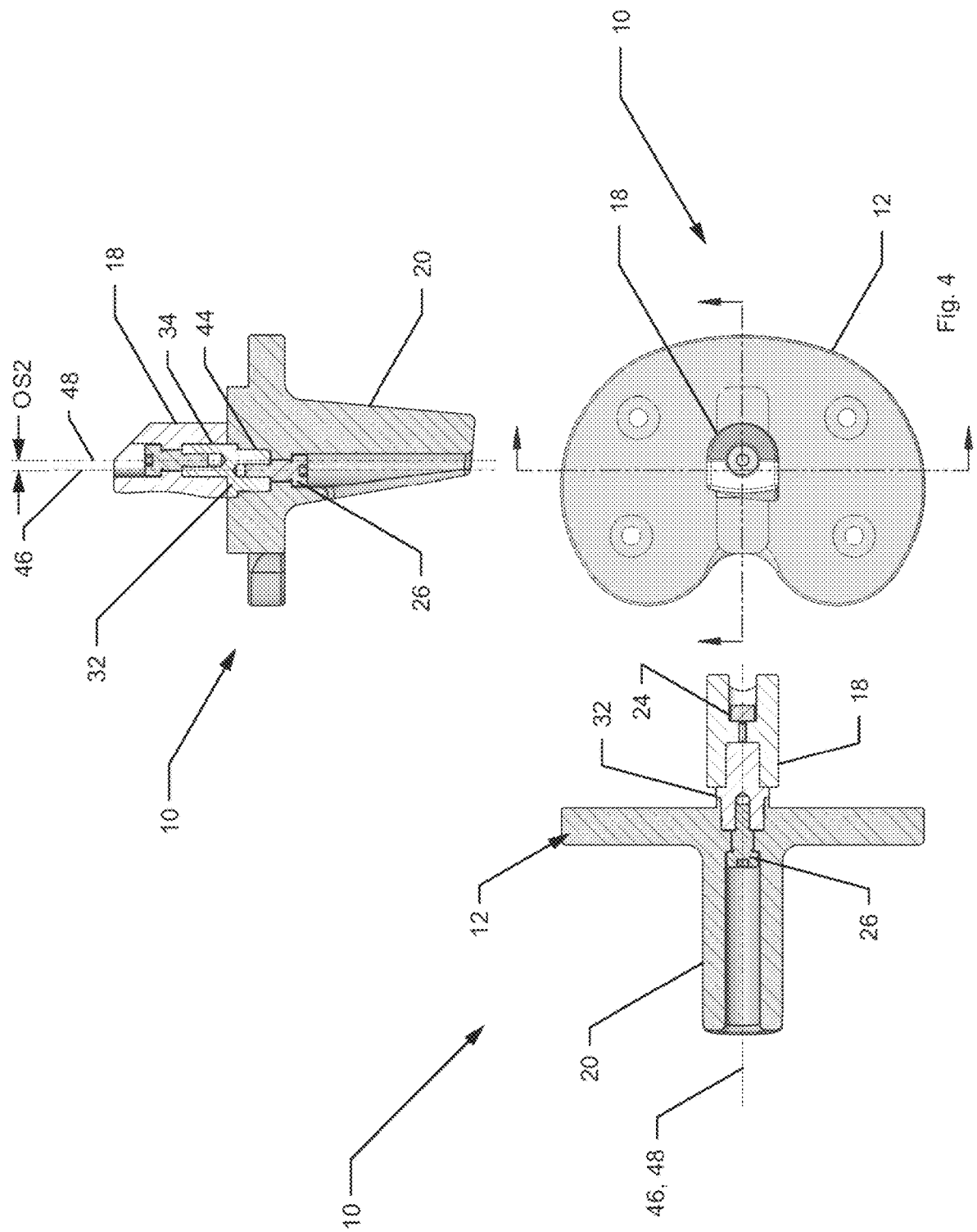
FIG. 4 shows three views of the tibial-tray system shown in FIG. 1 having an anterior-offset adapter.

In the embodiment shown in FIG. 4, the tibial-tray system 10 is fitted with an anterior-offset adapter 32. More specifically, a proximal end 34 of the adapter 32 defines a first superior-inferior axis 48, and a distal end 44 of the adapter 32 defines a second superior-inferior axis 46. The first superior-inferior axis 48 is offset by a distance of OS2, which in this embodiment is 2 mm in the anterior direction. Similar to the views shown in FIG. 3, the upper view in FIG. 4 shows a section of the tibial-tray system 10 viewed in a sagittal plane, while the left most view is a section viewed in a coronal plane. As shown in the left most view, the first and second superior-inferior axes are coincident, indicating that the adapter 32 is neutral in the M-L direction.

Although these embodiments use an adapter 28 with a 2 mm posterior offset (FIG. 3) and an adapter 32 with a 2 mm anterior offset (FIG. 4), it is understood that other embodiments may have offsets of more or less than 2 mm, and they may be offset in either the anterior or posterior direction—or even in the medial or lateral direction if desired. Of course, adapters used with tibial-tray system such as described herein may be "neutral"—i.e., having no offset—such as illustrated in FIGS. 2 and 5.

FIG. 5 shows top and side views of the adapter 22—see also FIG. 1. As shown in FIG. 5, the distal end 25 has a generally circular cross section, but has a slight taper on its outer surface—e.g., a Morse taper. As described above, this allows the distal end 25 to mate with a corresponding tapered hole in a tibial tray, such as the tibial tray 20. Each of the ends 23, 25 includes a threaded hole 36, 38 configured to receive a threaded fastener such as the fasteners 24, 26. The adapter 22 also includes a platform, which in this embodiment is a shoulder 40, positioned between the proximal and distal ends 23, 25. The platform 40 includes a proximal face 37 having a proximal member—e.g., the proximal end 23—extending therefrom. The platform 40 also includes a distal face 39 having a distal member—e.g., the distal end 25—extending therefrom. As explained in more detail below, the adapter 22 is configured such that a relative position between the proximal member 23 and the distal member 25 disposes the spline 18 at a predetermined position relative to the tibial tray 12 when the adapter is attached to the spline 18 and the tibial tray 12.

As described above, the adapter 22 is a neutral-position adapter, which means that a superior-inferior axis 41 of the proximal end 23 is coincident with a superior-inferior axis 43 of the distal end 25 when viewed in a sagittal plane or a coronal plane. As described below, some adapters in accordance with embodiments described herein have an offset between the superior-inferior axes of their proximal and distal ends. If there is an offset between these axes when viewed in a sagittal plane, the adapter has an A-P offset, and if the offset appears when viewed in a coronal plane, the adapter has an M-L offset. Some adapters may have both an A-P offset and an M-L offset.

having the center lines 41, 43 of the respective proximal and distal ends 23, 25 coincident with each other. In contrast, FIG. 6 shows top and side views of the anterior-offset adapter 32—see also FIG. 4. Although some features of the adapter 32 are the same or similar as those of the adapter 22—e.g., the distal end 44 is tapered to mate with a tibial tray—there are differences. The most notable of these is that the centerline 46 of the distal end 44 is offset from the centerline 48 of the proximal end 34 by the distance OS2. In this embodiment, the OS2 offset is 2 mm, although other adapters may have different offsets as described above.

Adapters, such as the adapters 22, 32 may be manufactured to different sizes and with different configurations as described below. Even so, the adapters 22, 32 shown in FIGS. 5 and 6 have the same or similar dimensions for several of their features. Using the adapter 22 as an example, the proximal end 23 may have a height (h1) of approximately 0.35 inches (in.); in other embodiments, the proximal end 23 may have a height in the range of 0.25 in. to 1.0 in., or even outside of this range. The distal end 25 may have a height of approximately 0.25 in., although in other embodiments, it may have a height in the range of 0.25 in. to 1.0 in., or even outside of this range. In the embodiment shown in FIG. 5, the shoulder 40 is about 0.8 in. high (h3), although in other embodiments it may be in a range of 0.08 in. to 1.0 in. high, or even outside of this range.

As shown in FIG. 5, the shoulder 40 is rectangular—see the top view—and may have sides with length dimensions (d1), (d2) that are both approximately 0.4 in., although in other embodiments, these lengths may be in the range of 0.25 in. to 1.0 in., or even outside of this range. Similarly, the proximal end 23 of the adapter 22 has a rectangular shape and may have sides with length dimensions (d3), (d4) that are both approximately 0.25 in., although in other embodiments, these lengths may be in the range of 0.125 in. to 0.6 in., or even outside of this range. The distal end 25, however, is generally circular, and as described above, is tapered to mate with a tapered hole in a tibial tray. The proximal and distal ends, while described as square in this embodiment, may be rectangular with sides of different lengths, they may be circular, or they may have other geometric shapes as needed or desired for the particular application.

FIG. 7 shows three views of the spline 18, which includes a chamfered surface 50 on the anterior side of its proximal end. The spline 18 also includes a rectangular aperture 52 in its distal end, which is configured to receive a proximal end of an adapter, such as the proximal end 23 of the adapter 22. A round aperture 54 is provided in the proximal end of the spline 18 and is configured to receive a threaded fastener, such as the fastener 24 shown in FIG. 2. The spline 18 includes a posterior surface 56, which in this embodiment, includes a distal asymmetric eminence 58 projecting outwardly in the posterior direction. As shown in the top view in FIG. 7, the distal eminence 58 is disposed on only one of the medial or lateral sides. This may provide a more anatomical movement of the knee as it extends and flexes. In other embodiments, a spline, such as the spline 18, may be provided with different levels of constraint by changing its height, width, thickness, or some combination of these. Changing these geometric parameters can provide a desired constraint within the cruciate-sacrificing, mating box feature of the femoral component.

Figure 8:
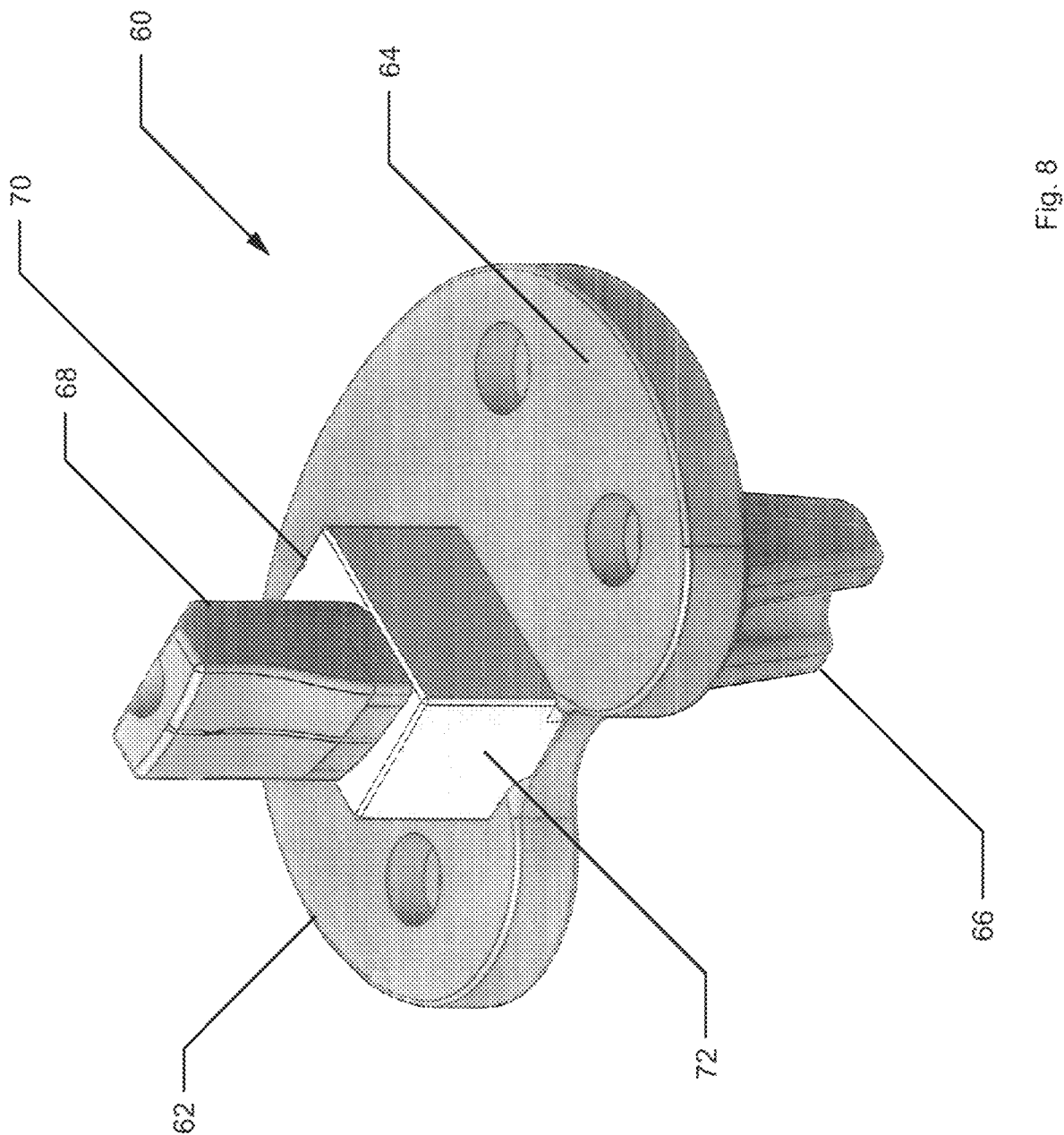
FIG. 8 shows a tibial-tray system in accordance with embodiments described herein, including an adapter with a raised central platform.

FIG. 8 shows a tibial-tray system 60 in accordance with embodiments described herein. The tibial-tray system 60 includes a tibial tray 62 having a proximal surface 64 and a distally extending post 66. A spline 68 is positioned on an adapter 70, which, as explained in more detail below, includes a proximally extending platform 72. FIG. 9 shows a top and two sectional views of the tibial-tray system 60. A proximal end 74 of the adapter 70 is configured to cooperate with an aperture 75 in a distal portion of the spline 68. In this embodiment, the spline 68 is secured to the adapter 70 by a threaded fastener 76. As described in more detail below, embodiments may include a spline and adapter configuration that allows the spline to rotate relative to the adapter, piston up and down relative to the adapter, or both.

Although the adapter 70 has an A-P offset, as shown by the distance (OS3) between the proximal end 74 and a distal end 78, in this embodiment it is really "neutral" because an aperture 79 in the tibial tray 62 is itself offset from a neutral position. Therefore, when the adapter 70 is installed in the tibial tray 62, the proximal end 74 will be in a neutral position relative to the rest of the knee system. This illustrates another advantage of tibial-tray systems as described herein: the adapter can be configured to accommodate many different styles of trays, which provides the surgeon more options and greater flexibility for choosing the best implant for the patient.

Similar to the other embodiments described above, the distal end 78 of the adapter 70 is configured with a Morse taper to secure it to the tibial tray 62. The distal end 78 can be provided with one mating feature, two mating features, or more as needed or desired for the particular application. For example, even though the distal end 78 of the adapter 70 is configured with a taper fit, another threaded fastener 80 is used to further secure the adapter 70 to the tibial tray 62. As described above, the adapter 70 includes a raised platform 72, which allows the spline 68 to be elevated from the proximal surface 64 of the tibial tray 62. As shown in FIG. 9, the platform 72 is positioned in a recess 82 in the surface 64 of the tibial tray 62. Embodiments of adapters can be configured with platforms having different heights—i.e., different distances from the proximal surface 84 of the platform 72 to the proximal surface 64 of the tibial tray 62; see, e.g., the dimension (h4) in FIG. 11. In this way, a spline, such as the spline 68, can be positioned at different heights relative to the tibial tray to accommodate tibial inserts of different thicknesses. As described above, maintaining an inventory of adapters having platforms of different heights is much more efficient and cost-effective than maintaining an inventory of splines having different heights. This is because, at least in some embodiments, the adapters will be made from a metal alloy that can be resterilized after a package is opened in surgery; whereas, splines, such as the spline 68, may be manufactured from a polymeric material that cannot be resterilized once the original sterile packaging is opened.

Similar to the other embodiments described above, adapters having platforms of different heights can be manufactured with different A-P offsets, including a zero offset, or neutral position. As described above, the adapter 70 shown in FIG. 9 is a neutral-position adapter, and is compared to two different offset adapters in FIGS. 10-12. Specifically, the adapter 70 is shown in FIG. 11, while a posterior-offset adapter 86 is shown in FIG. 10. Similarly, an anterior-offset adapter 88 is shown in FIG. 12. In each of these embodiments, the adapters 70, 86, 88 are configured to mate with a tibial tray through a round, tapered end, which can be further secured with a fastener, such as a threaded fastener. They are also configured to mate with a spline through a rectangular proximal end which may also be further secured with a fastener. Like the adapter 70, the adapters 86, 88 are configured for use with a tibial tray, such as the tibial tray 62, having an aperture that is offset; therefore, their offsets may appear greater than other adapters having the "same" offset—such as +2 mm or −2 mm—but when they are attached to a mating tibial tray, the resulting position of the proximal portion of the spline relative to the rest of the knee system will be the same as with these other adapters.

Figure 13:
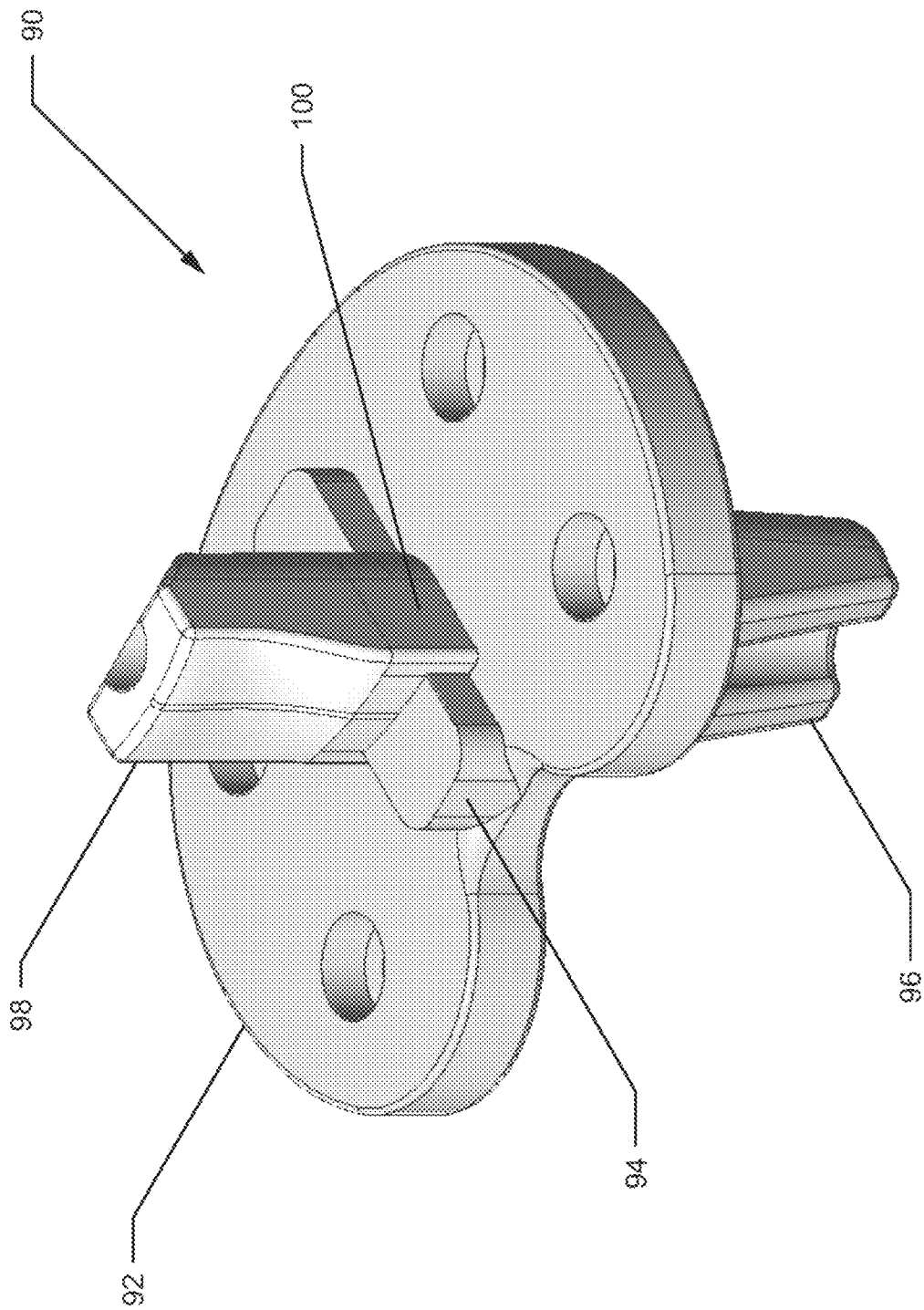
FIG. 13 shows a perspective view of a tibial-tray system in accordance with embodiments described herein.

FIG. 13 shows a tibial-tray system 90 in accordance with embodiments described herein. The tibial-tray system 90 includes a tibial tray 92, which has a raised central platform 94 extending proximally, and a distally extending post 96. The tibial-tray system 90 also includes a spline 98. Although the spline 98 has similarities to other splines illustrated and described above, the spline 98 has a distal end 100 that straddles the raised central portion 94 of the tibial tray 92. Even though it is not visible in FIG. 13, the spline 98 is secured to the tibial tray 92 through an adapter 102—see FIG. 14.

Figure 14:
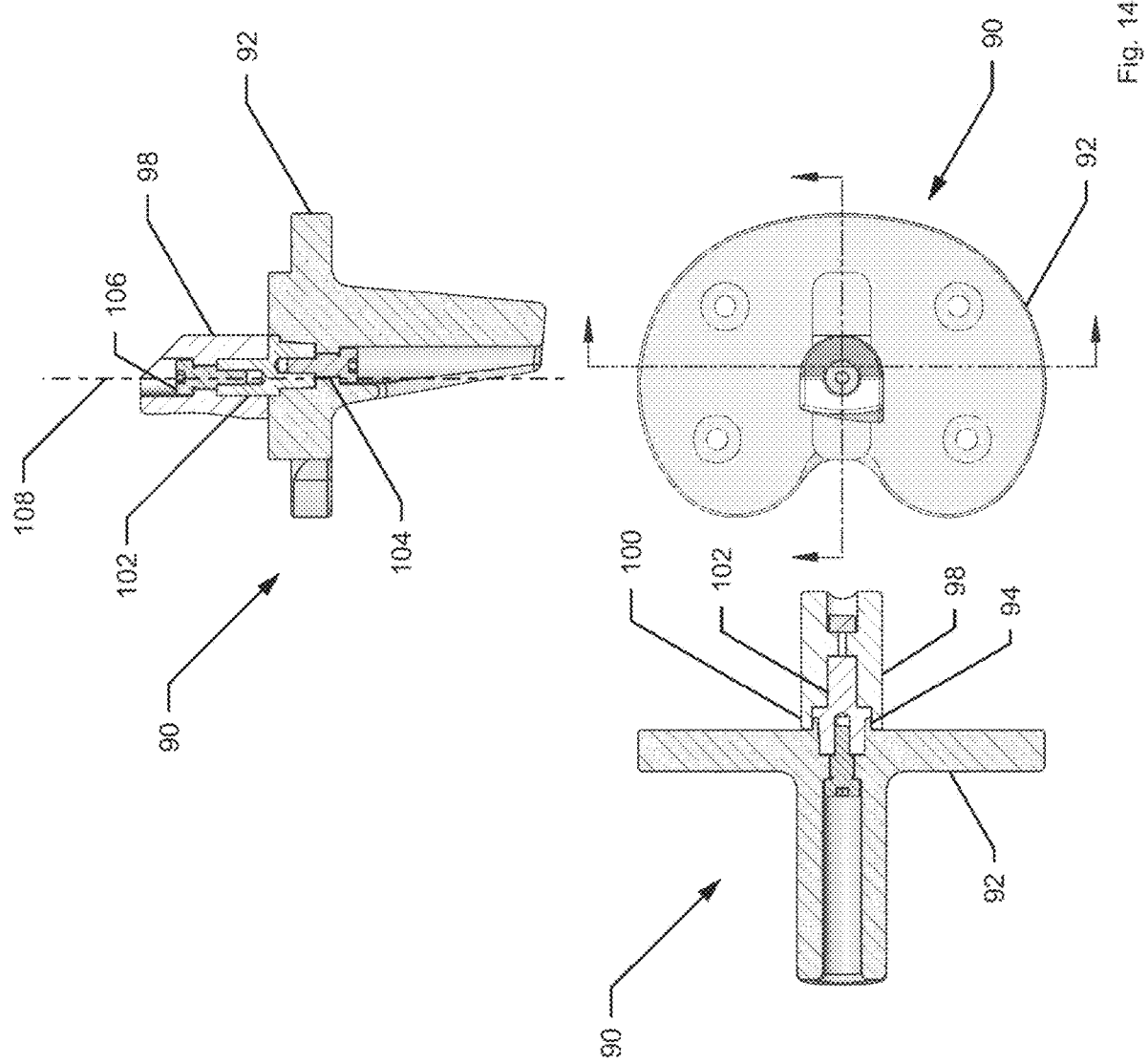
FIG. 14 shows three views of the tibial-tray system shown in FIG. 13 having a posterior-offset adapter.

FIG. 14 shows three views of the tibial-tray system 90, including two sectional views. As shown in FIG. 14, the adapter 102 is offset slightly to a posterior side of the tibial tray 92. In this embodiment, it is a 2 mm posterior offset from the neutral position, although in other embodiments, adapters having different posterior or anterior offsets, including no offset, may be used. Similar to the embodiments illustrated and described above, the adapter 102 is secured to the tibial tray 92 through a tapered fit and a threaded fastener 104. Similarly, the spline 98 is secured to the adapter 102 with a threaded fastener 106 positioned along a superior-inferior axis 108.

As best illustrated in the left sectional view in FIG. 14, the distal end 100 of the spline 98 covers not only the raised central platform 94 of the tibial tray 92, but it also covers a portion of the adapter 102. This is in contrast to the tibial-tray system 10 described above, in which a portion of the adapter 22 is positioned above the raised central platform 14, but is below the spline 18, which leaves a portion of it exposed—see, e.g., FIG. 2, and in particular, the left sectional view. It may be desirable to cover the adapter with the distal end of a spline, and the embodiment illustrated in FIGS. 13 and 14 provides this option.

Figure 15:
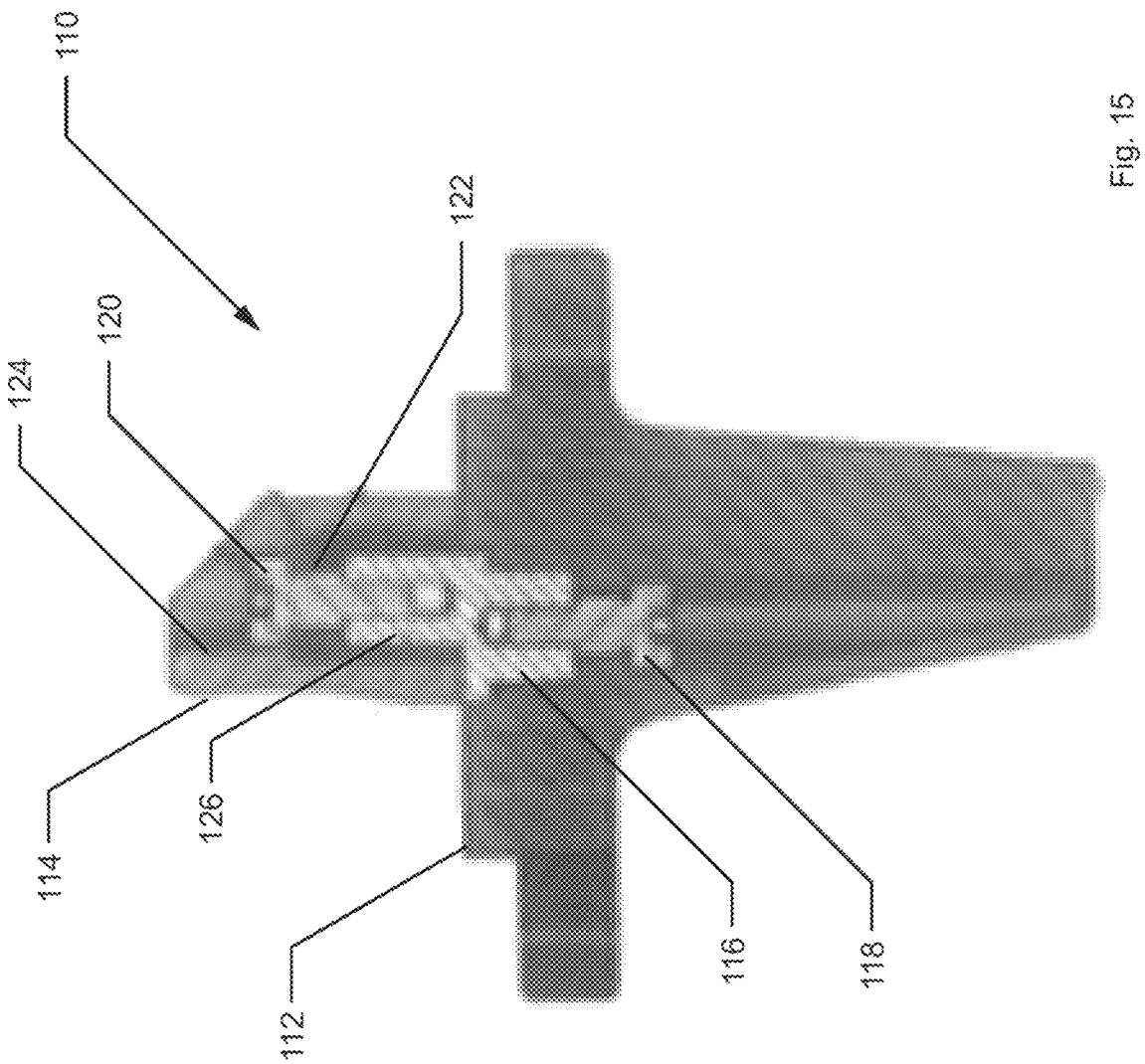
FIG. 15 shows a cross-sectional view of a tibial-tray system in accordance with embodiments described herein having a spline with a support structure.

FIG. 15 shows a tibial-tray system 110 in accordance with embodiments described herein. The system 110 includes a tibial tray 112, a spline 114, and an adapter 116 similar to the adapters described above—i.e., it may be configured with an A-P offset, an M-L offset, or it may be neutral and have no offset. The adapter 116 is secured to the tibial tray 112 with a threaded fastener 118 and is secured to the spline 114 with a threaded fastener 120. The spline 114 may be made from ceramic, metallic, or polymeric materials. In the embodiment shown in FIG. 15, the spline 114 includes a support structure 122 positioned inside an aperture 124 that is configured to allow the spline 114 to fit over a proximal end 126 of the adapter 116. The aperture 124 also provides an opening for the threaded fastener 120 to be inserted into the spline 114 to secure it to the adapter 116.

Because the clamping force exerted by the threaded fastener 120 may be significant—depending on the specific application—the spline 114 may benefit from the additional strength provided by the support structure 122. This may be particularly important if the spline 114 is made from a polymeric material, although support structures, such as the support structure 122, may be beneficial when the spline 114 is made from other materials, such as ceramics or even other metallic materials. The support structure 122 may be made from a material that is stronger than rest of the spline 114. For example, an exterior portion of the spline 114 may be made from a polymeric material, while the support structure 122, comprising an interior portion of the spline 114, may be made from a metallic or ceramic material. Like the spline 114, the support structure 122 may also be made from a polymeric material, but one that is stronger, harder, or both, than the polymer used for the outer portion of the spline 114.

FIG. 16 shows top and side views of a tibial-tray system 128 in accordance with embodiments described herein. The tibial-tray system 128 includes a tibial tray 130 and a spline 132. It also includes an adapter 134, which may be configured similarly to the adapters described above. In this embodiment, the adapter 134 is secured to the tibial tray 130 with a threaded fastener 136; however, absent from this embodiment is any fastener securing the spline 132 to the adapter 134. In this embodiment, the spline 132 and a proximal portion 138 of the adapter 134 may have a sliding or slight interference fit. This allows the spline 132 to move up and down—i.e. "piston"—in the superior-inferior directions as indicated by the "S-I" line 140. The spline 132 is also capable of rotational movement around the proximal portion 138 of the adapter 134 as indicated by the rotational directional arrow 142. In this embodiment, the spline 132 is also able to move relative to the tibial tray 130 in the anterior-posterior direction as indicated by the "A-P" line 144. Similarly, the spline 132 can move and be adjusted relative to the tibial tray 130 in the medial-lateral direction as indicated by the "M-L" line 146.

The embodiment shown in FIG. 16 also includes a "smart component" 145 positioned within an opening 147 in the adapter 134. The smart component 145 may include, for example, a microcontroller having one or more processors, memory, and the ability to receive inputs and provide outputs, for example, related to the tibial-tray system 128. The smart component 145 may also include a power source to allow it to perform various tasks, such as receiving inputs from positional sensors positioned in or around the tibial-tray system 128 and providing outputs external to the patient indicating the position of parts of the tibial-tray system 128 or other information. The smart component 145 may be part of a feedback control loop that provides information to the patient and medical personnel. The use of the adapter 134 provides a convenient location for the smart component 145 and eliminates the need to change the geometry of the tibial-tray system to accommodate these features.

The smart component 145 may also contain a global-positioning system (GPS), an accelerometer, or some combination of these, to track the relative position or motion of the smart component 145 or other components of the tibial-tray system 128. In this embodiment, the smart component 145 is positioned within the adapter 134, but in other embodiments, it may be positioned within other components of the tibial-tray system 128. And in some embodiments, more than one smart component, such as the smart component 145, may be used—e.g., a smart component may be positioned within the adapter 134 and within the tibial tray 130. These smart components may be used in a trial tibial-tray system to provide information to a surgeon before the final device is implanted, or they may be used in the final device to provide information on an ongoing basis.

A spline, such as the spline 132 and the other splines described above, can be configured with a geometry to assist the motion of a femoral component as a patient alternately flexes and extends his or her knee. Specifically, a spline can be configured to help ensure that the interaction of the femoral component with the tibial-tray system emulates natural kinematics. When a femoral component is placed on a tibial-tray system that includes a spline, the condyles and other physical features of the femoral component form a generally rectangular boundary around the spline. This may be conveniently referred to as a "femoral-cruciate box", and it is illustrated and described below in conjunction with FIGS. 23-25. In FIG. 17, a spline 148—which may be used in conjunction with some or all the embodiments described herein—is configured with two relief areas 150, 152. The relief areas 150, 152 do not extend for the entire height of the spline 148, but rather begin at a position below an upper, proximal surface 154 of the spline 148.

FIG. 18 shows top, front, and side views of the spline 148. The top view provides the orientation of the spline 148 with the anterior (A), posterior (P), medial (M), and lateral (L) sides being labeled. As shown in the front and side views, the relief areas 150, 152 increase in width (W1) and depth (D1) into the spline 148 as they move downward—i.e., distally. Stated another way, the relief areas 150, 152 have a greater width and depth at a distal position on the relief area than at a proximal position on the relief area. This is further illustrated in FIG. 19, which shows three sectional views taken through the cut lines A-A, B-B, and C-C from the front view in FIG. 18. The relief areas 150, 152 interact with the femoral-cruciate box to allow the femoral component to gradually increase rotation around the spline 148 as a patient transitions from standing extension (Section A-A, where there is no relief area) to full flexion (Section C-C, where the relief areas 150, 152 are the largest). Embodiments of tibial-tray systems described herein may include relief areas having different geometries from the relief areas 150, 152 as more or less rotation is desired.

As described above, a spline may include one or more eminences—i.e., protrusions—from a surface or surfaces of the spline. These protrusions may be in addition to relief areas such as described above with regard to the spline 148, or they may be on a spline having no relief areas. FIG. 20 shows a spline 156 that includes relief areas 158, 160, and also includes protrusions 162, 164—see also FIG. 21. As shown in the top view of FIG. 21, the protrusions 162, 164 are respectively disposed on the anterior and posterior sides of the spline 156. Similar to the relief areas 150, 152 on the spline 148, the relief areas 158, 160 do not extend for the entire height of the spline 156. The same is true for the protrusions 162, 164, which begin approximately one third of the way down from an upper surface 166 of the spline 156.

Figure 22:
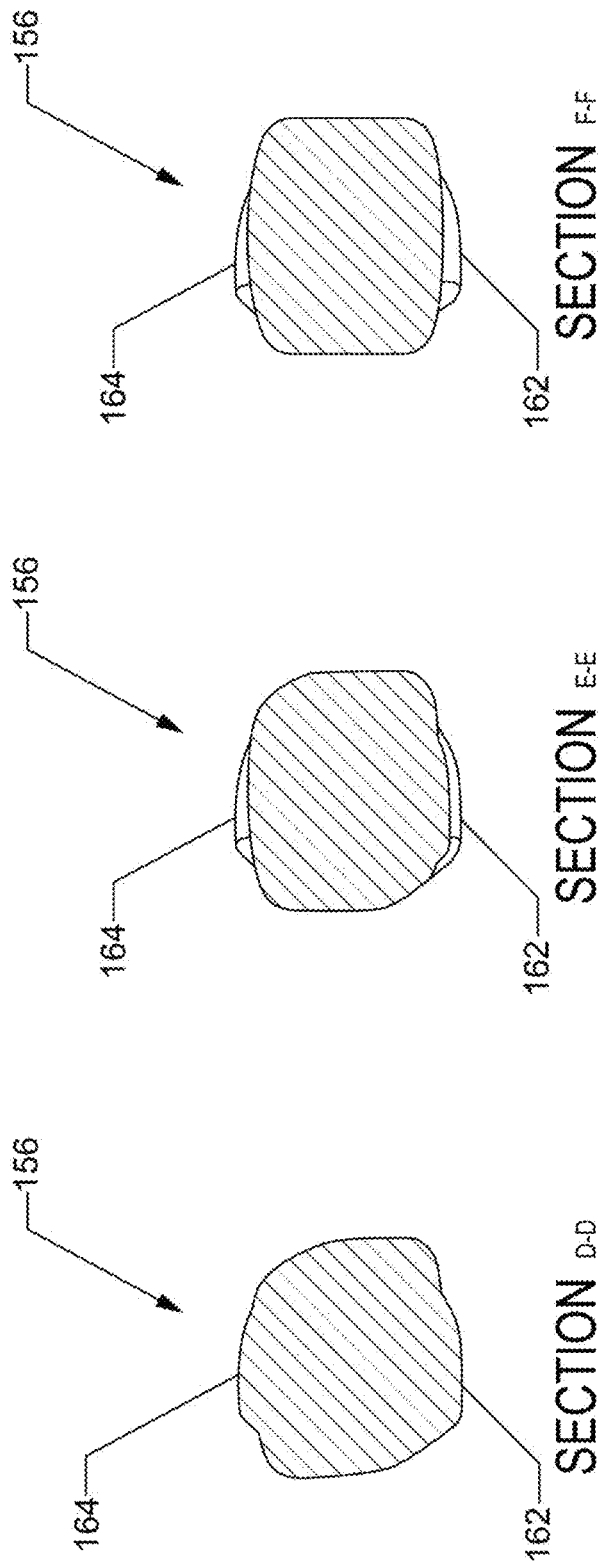
FIG. 22 shows three sectional views of the spline shown in FIG. 21.

As shown in FIGS. 20 and 21, the protrusions 162, 164 gradually increase in width (W2) and thickness (D2) in a distal direction toward the bottom of the spline 156. The protrusions 162, 164 are not symmetrical in the medial-lateral direction, and similarly do not extend across the full medial-lateral dimension of the spline 156. The anterior protrusion 164 begins slightly off the centerline of the spline 156 and gradually increases in the medial and distal directions. The posterior protrusion 162 also begins slightly off the centerline of the spline 156, but it increases in size in the lateral and distal directions. Stated another way, the protrusions have a greater width and thickness at a distal position on the protrusion than at a proximal position on the protrusion. This is further illustrated in FIG. 22, which shows three sectional views taken through the cut lines D-D, E-E, and F-F from the front view in FIG. 21. The posterior protrusion 162 causes the tibia to rotate internally with respect to the femur during flexion, while the anterior protrusion 164 causes the tibia to rotate externally with respect to the femur during extension.

Figure 23A:
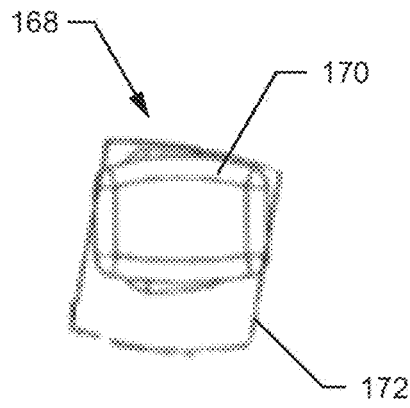
FIG. 23A and FIG. 23B show the interaction of a femoral component with a spline in accordance with embodiments described herein when the knee is hyperextended.
Figure 23B:
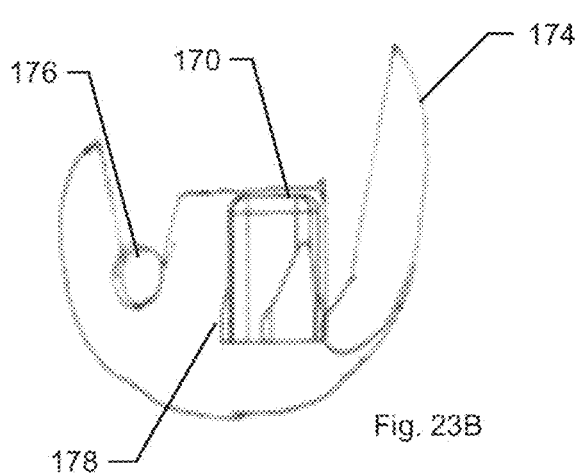

As described above, the interface between the condyles and other physical features of the femoral component and a spline forms a generally rectangular boundary around the spline, or a "femoral-cruciate box". This interaction is illustrated in FIGS. 23-25. More specifically, FIG. 23A shows a portion of the tibial-tray system 168 in accordance with embodiments described herein. Shown in FIG. 23A is a top view of a spline 170 and the outline 172 of the inner walls of a femoral component 174 shown in FIG. 23B. The outline 172 is a line representation of what was referred to above as the femoral-cruciate box. FIGS. 23A and 23B are representative of the position of the femoral component 174 relative to the spline 170 when the knee is hyperextended. As shown in FIG. 23A, the sides of the femoral-cruciate box 172 are not aligned with the sides of the spline 170; rather, the sides of the femoral-cruciate box 172 are rotated relative to the sides of the spline 170. And as shown in FIG. 23B, the femoral component 174 includes a post 176 that traverses in a medial—lateral direction across the condyles of the femoral component 174. In hyperextension, the post 176 does not contact the spline 170, but as described below, it will as the knee is placed in flexion.

Figure 24A:
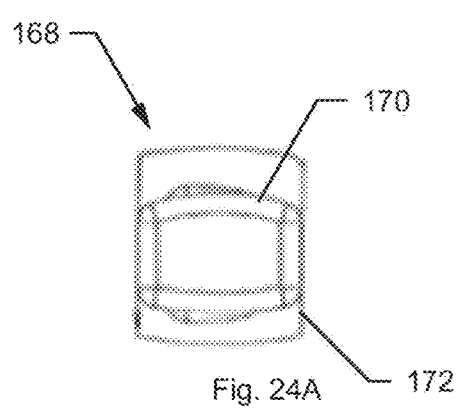
FIG. 24A and FIG. 24B show the interaction of a femoral component with a spline in accordance with embodiments described herein when the knee is in mid-gate rotation.
Figure 24B:
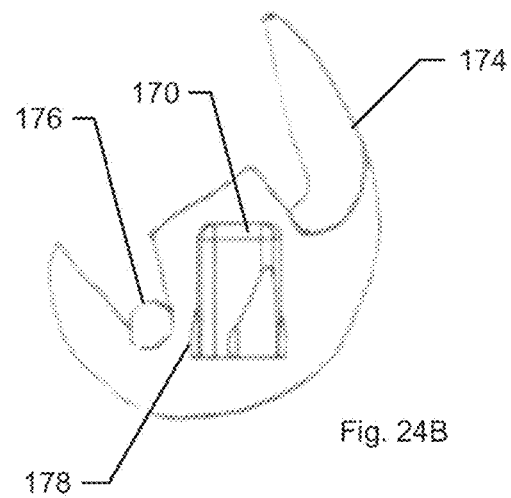
Figure 25A:
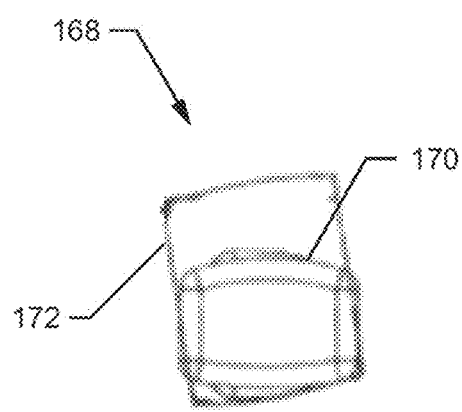
FIG. 25A and FIG. 25B show the interaction of a femoral component with a spline in accordance with embodiments described herein when the knee is in deep flexion.
Figure 25B:
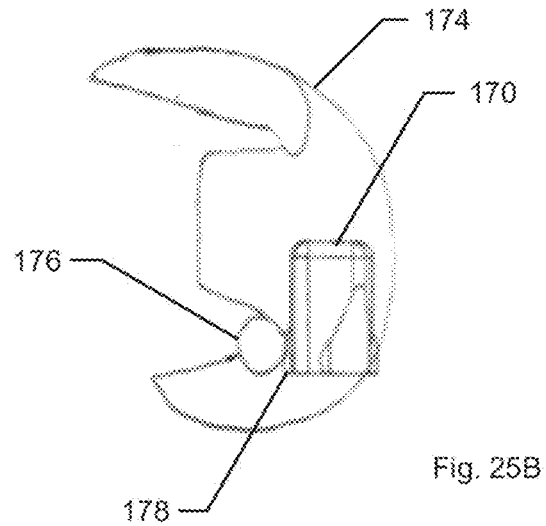

FIGS. 24A and 24B show the relative positions of the femoral-cruciate box 172 and the spline 170 when the knee is in mid-gate rotation. That is, as a patient is walking, and the knee transitions from hyperextension to deep-knee flexion, there will be a relative rotation between the femoral component 174 and the spline 170 in the sagittal plane—i.e., when viewed from the medial or lateral sides as shown in FIG. 24B. In this position, the post 176 has not yet reached the spline 170. As this rotation is occurring, there will also be a relative rotation between the femoral component 174 and the spline 170 in the transverse plane—i.e., when viewed in the superior to inferior direction (or vice versa). This is illustrated in FIG. 24A, which shows the walls of the femoral-cruciate box 172 to be generally aligned with the walls of the spline 170. Finally, when the knee has reached a position of deep flexion, the walls of the femoral-cruciate box 172 will again be rotated relative to the walls of the spline 170 as shown in FIG. 25A—although this is the opposite rotation from that shown in FIG. 23A when the knee is in hyperextension. When the knee has reached deep flexion, the post 176 will contact the distal portion of the spline 170, which includes a protrusion 178 similar to the spline 156 and its protrusion 162 shown in FIGS. 20-22.

As described above in conjunction with FIG. 16, embodiments of the tibial-tray systems described herein may include an adapter positioned between a tibial tray and a spline with an attachment between the adapter and the spline being configured to allow some motion of the spline relative to the adapter. A variation of this configuration is shown in FIG. 26, which illustrates a tibial-tray system 180 having a tibial tray 182, an adapter 184 and a spline 186. As shown in FIG. 26, the adapter 184 is secured to the tibial tray 182 with a threaded fastener 188. The spline 186 is also attached to the adapter 184 with a bolt 190 configured to allow some movement of the spline 186 relative to the adapter 184. At the opposite ends of the bolt 190 are a bolt head 192 and a threaded nut 194. In other embodiments, the positions of the bolt head 192 and the threaded nut 194 may be reversed, or fasteners other than a threaded nut may be used—and in some embodiments, the "bolt" 190 may be a stud secured with a threaded nut at each end. As shown in FIG. 26, there is a gap 196 (shown in white for clarity) between a proximal surface 198 of the spline 186 and the threaded nut 194. The size of the gap 196 can be controlled by the length of the bolt 190 and the position of the threaded nut 194. The gap 196 allows a controlled translation of the spline 186 relative to the adapter 184 along the superior-inferior axis 200. More specifically, the nut 194 provides a stop that limits movement of the spline 186 in the superior direction.

A variation of the embodiment shown in FIG. 26 is illustrated in FIG. 27, which shows a tibial-tray system 202 having a tibial tray 204, an adapter 206, and a spline 208. In this embodiment, the adapter 206 is secured to the tibial tray 204 with a threaded fastener 210. The spline 208 is also secured to the adapter with a threaded fastener 212, but as shown in FIG. 27, the threaded fastener 212 threads directly into the adapter 206 and therefore does not require a separate connector such as a threaded nut. Similar to the embodiment shown in FIG. 26, the threaded fastener 212 is positioned so there is a gap 214 between a proximal surface 216 of the spline 208 and a head 218 of the threaded fastener 212. The gap 214 allows a controlled translation of the spline 208 relative to the adapter 206 along the superior-inferior axis 220. And similar to the embodiments shown in FIGS. 16 and 26, an aperture 222 in the spline 208 is cylindrical with a round cross section. This allows the spline 208 to also rotate around the axis 220. In other embodiments, an aperture, such as the aperture 222, may have a square or other non-round cross section to inhibit rotation and limit movement of the spline 208 relative to the adapter 206 to only translation along the axis 220.

In the embodiment shown in FIG. 28, a tibial tray-system 224 includes a tibial tray 226, an adapter 228, and a spline 230. Similar to other embodiments described herein, the adapter 228 is attached to the tibial tray 226 with a threaded fastener 232—although other attachment mechanisms may be employed with this and the other embodiments, such as a tapered fit, a press-fit, etc. Unlike the embodiments illustrated in FIGS. 26 and 27, the embodiment shown in FIG. 28 does not include a separate fastener to attach the spline 230 to the adapter 228. Rather, the adapter 228 itself has an elongated member 234 extending proximally from a surface 236 through an aperture 238 in the spline 230. Similar to the embodiments illustrated in FIGS. 26 and 27, the spline 230 may be fitted to the elongated member 234 with a sliding fit or even slight interference fit to allow the spline 230 to translate along the superior-inferior axis 240. If the aperture 238 in the spline 230 is cylindrical with a round cross section, the spline 230 may also rotate around the elongated member 234. In other embodiments, however, the elongated member 234 may have a square or other shaped cross section to constrain the spline 230 so that it does not rotate about the superior-inferior axis 240.

FIG. 29 shows another embodiment of the tibial-tray system 242 accordance with embodiments described herein. The tibial-tray system 242 includes a tibial tray 244, an adapter 246, and a spline 248. The adapter 246 is secured to the tibial tray 244 with a threaded fastener 250. A different type of attachment arrangement, however, is provided for the spline 248. Specifically, the adapter 246 includes an aperture 252 disposed through a proximal portion of the adapter 246. In this embodiment, the aperture 252 is generally a slot having an oval shape. Connecting the spline 248 to the adapter 246 is an elongated member, which in this embodiment is a pin 254, positioned through the spline 248 and through the aperture 252 in the adapter 246. This configuration allows some limited translation and rotation of the spline 248 relative to the adapter 246 along and around the superior-inferior axis 256. This movement is schematically illustrated in FIG. 30, which is a view looking from a proximal end 258 to a distal end 260 of the spline 248 along the axis 256. The shape of the aperture 252, and the size and shape of the pin or clip 254, can be modified to provide more or less movement as desired.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A tibial-tray system, comprising:
   a tibial tray having a tapered aperture;
   a spline configured to extend proximally from the tibial tray and guide a femoral component of a knee system, the spline including a rectangular aperture at a distal end thereof; and
   an adapter having a tapered distal end configured to be received in the tapered aperture for attachment to the tibial tray, and a rectangular proximal end configured to be received through the rectangular aperture for attachment to the spline, the distal end having a position relative to a position of the proximal end such that the spline extends upward from the tibial tray at a predetermined position when the distal end of the adapter is attached to the tibial tray and the proximal end of the adapter is attached to the spline, wherein the proximal end of the adapter is configured to facilitate superior-inferior movement of the spline when the spline is attached to the proximal end of the adapter.

2. The tibial-tray system of claim 1, wherein the proximal end of the adapter defines a first superior-inferior axis and the distal end of the adapter defines a second superior-inferior axis, the first superior-inferior axis being coincident with the second superior-inferior axis when viewed in a sagittal plane.

3. The tibial-tray system of claim 1, wherein the proximal end of the adapter defines a first superior-inferior axis and the distal end of the adapter defines a second superior-inferior axis, the first superior-inferior axis being offset from the second superior-inferior axis by a predetermined distance when viewed in at least one of a sagittal plane or a coronal plane.

4. The tibial-tray system of claim 1, wherein at least one of the distal end of the adapter or the proximal end of the adapter further includes an aperture configured to receive a threaded fastener.

5. The tibial-tray system of claim 1, wherein the adapter includes a platform configured to extend proximally from a proximal surface of the tibial tray and to receive the spline thereon.

6. The tibial-tray system of claim 5, wherein the spline includes a distally extending portion configured to cover at least a portion of the platform.

7. The tibial-tray system of claim 1, wherein the proximal end of the adapter is attached to the spline such that movement of the spline is limited in a superior direction.

8. The tibial-tray system of claim 1, wherein the spline includes an exterior portion made from a first material configured to contact the femoral component of the knee system and an interior portion having a support structure disposed therein, the support structure being made from a second material different from the first material.

9. The tibial-tray system of claim 1, wherein the adapter includes a microcontroller disposed therein, the microcontroller including at least one processor and configured to receive inputs and provide outputs related to the tibial-tray system.

10. The tibial-tray system of claim 1, wherein the spline includes a relief area extending inwardly into the spline and having a greater width and depth at a distal position on the relief area than at a proximal position on the relief area.

11. The tibial-tray system of claim 1, wherein the spline includes a protrusion extending outwardly from the spline and having a greater width and thickness at a distal position on the protrusion than at a proximal position on the protrusion.

12. The tibial-tray system of claim 1, wherein the proximal end of the adapter includes an aperture disposed therethrough in a direction transverse to a superior-inferior axis, the tibial-tray system further including an elongated member disposed through the spline and aperture such that the spline is movably attached to the proximal end of the adapter.

13. A tibial-tray system, comprising:
   a tibial tray having a tapered aperture;
   a spline configured to extend proximally from the tibial tray and guide a femoral component of a knee system, the spline having an interior portion with a rectangular aperture at a distal end thereof; and
   an adapter including a platform having a proximal face with a rectangular proximal member extending therefrom and a distal face with a tapered distal member extending therefrom, the rectangular proximal member being configured to be received through the rectangular aperture for attachment to the spline, and the tapered distal member configured to be received in the tapered aperture for attachment to the tibial tray, and wherein the adapter is configured such that a relative position between the proximal member and the distal member disposes the spline at a predetermined position relative to the tibial tray when the adapter is attached to the spline and the tibial tray, wherein a proximal end of the adapter is configured to facilitate superior-inferior movement of the spline when the spline is attached to the proximal end of the adapter.

14. The tibial-tray system of claim 13, wherein the proximal member of the adapter defines a first superior-inferior axis and the distal member of the adapter defines a second superior-inferior axis, the first superior-inferior axis being coincident with the second superior-inferior axis when viewed in at least one of a sagittal plane or a coronal plane.

15. The tibial-tray system of claim 13, wherein the proximal member of the adapter defines a first superior inferior axis and the distal member of the adapter defines a second superior-inferior axis, the first superior-inferior axis being offset from the second superior-inferior axis by a predetermined distance when viewed in at least one of a sagittal plane or a coronal plane.

16. A tibial-tray system, comprising:
a tibial tray having a tapered aperture;
a spline configured to extend proximally from the tibial tray and guide a femoral component of a knee system, the spline including an interior portion with a rectangular aperture at a distal end thereof; and
an adapter configured to be positioned between the tibial tray and the spline such that a rectangular first portion of the adapter is configured to be received through the rectangular aperture and attachable to the spline, and a tapered second portion of the adapter is configured to be received in the tapered aperture and attachable to the tibial tray to dispose the spline at a predetermined position relative to the tibial tray when the adapter is attached to the spline and the tibial tray, wherein a proximal end of the adapter is configured to facilitate superior-inferior movement of the spline when the spline is attached to the proximal end of the adapter.

17. The tibial-tray system of claim 16, further comprising a plurality of the adapters, and wherein each proximal end of the adapters defines a respective first superior-inferior axis and each distal end of the adapters defines a respective second superior-inferior axis, and wherein the first superior-inferior axis of a first one of the adapters is coincident with the second superior-inferior axis of the first one of the adapters when viewed in a sagittal plane, and the first superior-inferior axis of a second one of the adapters is offset from the second superior-inferior axis of the second one of the adapters when viewed in a sagittal plane.

18. The tibial-tray system of claim 16, further comprising a plurality of the adapters, and wherein each proximal end of the adapters defines a respective first superior-inferior axis and each distal end of the adapters defines a respective second superior-inferior axis, and wherein the first superior-inferior axis of a first one of the adapters is coincident with the second superior-inferior axis of the first one of the adapters when viewed in a coronal plane, and the first superior-inferior axis of a second one of the adapters is offset from the second superior-inferior axis of the second one of the adapters when viewed in a coronal plane.

\* \* \* \* \*